United States Patent
Li

(10) Patent No.: US 9,481,884 B2
(45) Date of Patent: Nov. 1, 2016

(54) ENABLING THE USE OF LONG DSRNA FOR GENE TARGETING IN MAMMALIAN AND OTHER SELECTED ANIMAL CELLS

(71) Applicant: Chiang J. Li, Cambridge, MA (US)

(72) Inventor: Chiang J. Li, Cambridge, MA (US)

(73) Assignee: 1GLOBE BIOMEDICAL CO., LTD., Beijing (CN)

( * ) Notice: Subject to any disclaimer, the term of this patent is extended or adjusted under 35 U.S.C. 154(b) by 0 days.

(21) Appl. No.: 13/951,323

(22) Filed: Jul. 25, 2013

(65) Prior Publication Data

US 2013/0330824 A1 Dec. 12, 2013

Related U.S. Application Data

(63) Continuation of application No. 12/667,867, filed as application No. PCT/US2008/068866 on Jun. 30, 2008, now abandoned.

(60) Provisional application No. 60/947,311, filed on Jun. 29, 2007.

(51) Int. Cl.
  C12N 15/00 (2006.01)
  C12N 15/11 (2006.01)
  C12N 15/113 (2010.01)

(52) U.S. Cl.
  CPC ........... C12N 15/113 (2013.01); C12N 15/111 (2013.01); C12N 15/1135 (2013.01); C12N 2310/111 (2013.01); C12N 2310/141 (2013.01); C12N 2320/32 (2013.01)

(58) Field of Classification Search
  CPC .............................. C12N 15/113; C12N 15/63
  See application file for complete search history.

(56) References Cited

U.S. PATENT DOCUMENTS

| | | | |
|---|---|---|---|
| 6,060,241 A | 5/2000 | Corthesy-Theulaz | |
| 6,506,559 B1 * | 1/2003 | Fire et al. | 435/6.16 |
| 7,390,646 B2 * | 6/2008 | Andino-Pavlovsky et al. | 435/252.33 |
| 2002/0176848 A1 | 11/2002 | Sizemore et al. | |
| 2003/0061626 A1 | 3/2003 | Plaetinck et al. | |
| 2004/0191905 A1 | 9/2004 | Stevenson et al. | |
| 2005/0118193 A1 * | 6/2005 | Andino-Pavlovsky et al. | 424/200.1 |
| 2005/0233994 A1 | 10/2005 | Kaykas et al. | |
| 2005/0239728 A1 * | 10/2005 | Pachuk et al. | 514/44 |
| 2005/0255086 A1 | 11/2005 | Davidson et al. | |
| 2006/0093582 A1 | 5/2006 | Peterson et al. | |
| 2006/0189557 A1 | 8/2006 | Slack et al. | |
| 2006/0228800 A1 | 10/2006 | Lin et al. | |
| 2007/0020652 A1 | 1/2007 | Alvarado et al. | |

FOREIGN PATENT DOCUMENTS

| | | |
|---|---|---|
| WO | 9918221 A1 | 4/1999 |
| WO | 2004058948 A2 | 7/2004 |
| WO | 2005079236 A2 | 9/2005 |
| WO | 2006066048 A2 | 6/2006 |
| WO | 2006078880 A2 | 7/2006 |
| WO | 2006126040 A1 | 11/2006 |
| WO | 2006130976 A1 | 12/2006 |
| WO | 2007070483 A2 | 6/2007 |

OTHER PUBLICATIONS

Diallo et al. Oligonucleotides 13: 381-392, 2003.*
Strat et al. Nucleic Acid Research 2006, 34:3803-3810.*
Qian et al., "Expression and Purification of the Carboxyl Terminus Domain of Schizosaccharomyces pombe Dicer in *Escherichia coli*," Protein Pept Lett (2005) vol. 12, No. 4, 311-314.
Clemens et al., "Use of Double-stranded RNA Interference in *Drosophila* cell lines to Dissect Signal Transduction Pathways," Proc Natl Acad Sci (US) (2000) vol. 97, No. 12, 6499-6503.
Xiang et al., "Short Hairpin RNA-expressing Bacteria Elicit RNA Interference in Mammals," Nature Biotechnology (2006) vol. 24, No. 6, 697-702.
Alvarez et al., "Endogenous and synthetic microRNAs stimulate simultaneous, efficient, and localized regulation of multiple target in diverse species." The Plant Cell (May 2006) vol. 18, 1134-1151.
Du et al., "Design of expression vectors for RNA interference based on miRNAs and RNA splicing." The FEBS Journal (Dec. 2006) vo 273, No. 23, 5421-5427.
Scherr et al., "Gene silencing by small regulatory RNAs in mammalian cells." Cell Cycle (Feb. 2007) vol. 6, No. 4, 444-449.
Issa et al., "Development of methods of RNA interference in the sheep gastrointestinal parasite, Trichostrongylus colubriformis," Intl J for Parasitology (2005) vol. 35, No. 9, 935-940.
Timmons et al., "Ingestion of bacterially expressed dsRNAs can produce specific and potent genetic interference in Caenorhabditis elegans," Gene (2001) vol. 263, 103-112.
Zhao et al., "High-throughput screening of effective siRNAs from RNAi libraries delivered via bacterial invasion." Nature Methods (2005) vol. 2, No. 12, 967-973.
Fajac et al., "Recombinant *Escherichia coli* as a gene delivery vector into airway epithelial cells," J of Controlled Release (2004) vol. 97, No. 2, 371-381.
Li et al., "Delivery of RNA interference," Cell Cycle (Sep. 2006) vol. 5, No. 18, 2103-2109.

(Continued)

*Primary Examiner* — Brian Whiteman
(74) *Attorney, Agent, or Firm* — Duan Wu, Esq.; Milstein Zhang & Wu, LLC

(57) ABSTRACT

The present invention provides a method of enabling the use of long dsRNA for gene silencing in mammalian cells through bacteria, preferably non-pathogenic or therapeutic strains of bacteria. DNA that encodes long double-strand RNAs are transformed into bacteria and processed in the bacterial cells into a mixture of smaller RNA duplexes and then released into the cytoplasm of the target cells, resulting in modulation of gene expression in the target cells. The methods overcome the incompatibility between long strong dsRNA and mammalian cells by eliminating, or mitigating, the non-specific innate immune response. The eukaryotic cells can be mammalian cells or avian cells. The gene of interest can be a mammalian, avian, bacterial, eukaryotic, or viral gene.

28 Claims, 7 Drawing Sheets

(56) References Cited

OTHER PUBLICATIONS

Torrisani et al., "Enjoy the silence: the story of let-7 microRNA and cancer," Current Genomics (Jun. 2007), vol. 8, No. 4, 229-233.
Chang et al., "microRNAs in vertebrate physiology and human disease," Annu Rev Genomics Hum Genet (May 2007) vol. 8, No. 1, 215-239.
Li et al., "Therapeutic biology: checkpoint pathway activation therapy, HIV Tat, and transkingdom RNA interference," J of Cellular Physiology (Dec. 2006) vol. 209, 695-700.
Rossi et al., "RNAi as a treatment for HIV-1 infection," Biotechniques (Apr. 2006) vol. 40, No. S4, S25-S29.
Extended European Search Report dated Nov 15, 2011 issued in EP 08781214.5, the EP equivalent of parent application (14 pages).

* cited by examiner

```
                              SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: DNA primer

<400> SEQUENCE: 1
ggatctagaa tcagctacag cagc                                              24

<210> SEQ ID NO 2
<211> LENGTH: 24
<212> TYPE: DNA
<213> ORGANISM: Artificial Sequence
<220> FEATURE:
<223> OTHER INFORMATION: DNA primer

<400> SEQUENCE: 2
tcctctagag ggcaatctcc attg                                              24

<210> SEQ ID NO 3
<211> LENGTH: 96
<212> TYPE: DNA
<213> ORGANISM: Artificial Sequence
<220> FEATURE:
<223> OTHER INFORMATION: DNA oligonucleotide

<400> SEQUENCE: 3
acggatcctc ctttcagcaa aaaacccctc aagacccgtt tagaggcccc aagggggttat      60 gctagttatt gctcagcggt ggtctagagg atccac                                 96

<210> SEQ ID NO 4
<211> LENGTH: 96
<212> TYPE: DNA
<213> ORGANISM: Artificial Sequence
<220> FEATURE:
<223> OTHER INFORMATION: DNA oligonucleotide

<400> SEQUENCE: 4
gtggatcctc tagaccaccg ctgagcaata actagcataa ccccttgggg cctctaaacg       60
ggtcttgagg ggttttttgc tgaaaggagg atccgt                                 96

<210> SEQ ID NO 5
<211> LENGTH: 96
<212> TYPE: DNA
<213> ORGANISM: Artificial Sequence
<220> FEATURE:
<223> OTHER INFORMATION: DNA oligonucleotide

<400> SEQUENCE: 5
gcgtcgactc tagaccaccg ctgagcaata actagcataa ccccttgggg cctctaaacg       60
ggtcttgagg ggttttttgc tgaaaggagt cgaccg                                 96

<210> SEQ ID NO 6
<211> LENGTH: 96
```

```
<212> TYPE: DNA
<213> ORGANISM: Artificial Sequence
<220> FEATURE:
<223> OTHER INFORMATION: DNA oligonucleotide

<400> SEQUENCE: 6
cggtcgactc ctttcagcaa aaacccctc aagacccgtt tagaggcccc aaggggttat    60
gctagttatt gctcagcggt ggtctagagt cgacgc                            96
```

ENABLING THE USE OF LONG DSRNA FOR GENE TARGETING IN MAMMALIAN AND OTHER SELECTED ANIMAL CELLS

CROSS-REFERENCE TO RELATED APPLICATIONS

This application claims priority to and the benefit of U.S. patent application Ser. No. 12/667,867, which is a national phase application under 35 U.S.C. 371 of PCT application PCT/US2008/068866, filed Jun. 30, 2008 and which in turn, claims priority to U.S. provisional patent application Ser. No. 60/947,311 filed Jun. 29, 2007, the content of all of which applications are incorporated herein by reference in entirety.

BACKGROUND OF THE INVENTION

RNA interference (RNAi) is a catalytic mechanism of gene-specific silencing in eukaryotic organisms with profound implications for biology and medicine. However, the inducers of such a powerful mechanism of gene-targeting are very different in mammalian cells and in non-mammalian cells.

Long double-strand RNAs (dsRNAs) triggered potent sequence-specific gene silencing in *C. elegans* and *Drosophila Melanogaster*. In contrast, long dsRNAs induce sequence-nonspecific response in mammalian cells due to activation of interferon related pathways. RNAi mechanism was considered non-functional in mammalian cells until siRNA duplexes were discovered.

The use of short interfering RNA (siRNA) to selectively target messenger RNA (mRNA) for degradation results in the silencing or knock-down of the gene expressed through the degradation of target mRNA. siRNA are typically double-strand RNA (dsRNA) of 20-25 nucleotide long with a few unpaired overhang bases on each strand. Based on this model, molecular biology techniques using siRNA have emerged both as a research tool and a candidate for therapeutics (Dykxhoorn, Novina & Sharp. *Nat. Rev. Mol. Cell Biol.* 4:457-467 (2003); Kim & Rossi, *Nature Rev. Genet.* 8:173-184 (2007); de Fougerolle s, et al. *Nature Rev. Drug Discov.* 6:443-453 (2007)).

While being used widely for gene silencing in mammalian cells, siRNA has posed numerous problems that limit the potential of RNAi in biomedical research and development of RNA-therapeutics. Unlike long dsRNA in non-mammlain cells, designing siRNA has proven difficult. First, within a gene sequence, only a certain sequence motifs can serve as template for siRNA. Identification of such motifs has been nearly a process of trials and errors despite of numerous algorithms developed over the years. Second, unlike long dsRNA in non-mammalian cells, siRNA has by and large low gene-silencing efficiency in mammalian cells (Reynolds A et al. *Nature Biotech* 22:326, 2004; A. de Fougerolles et al, *Nat Rev Drug Discov* 6, 443 (2007).). Finding a highly efficacious siRNA motif along an mRNA is difficult, and can be impossible for some mRNAs, due to nearly unlimited possible motifs of 20-25 nt contained in an mRNA. Third, after an siRNA is designed, delivery of negatively charged siRNA into mammalian cells has proven a daunting challenge (Li C X, et al. *Cell Cycle* 5:2103-2109 (2006)).

It would be highly desirable if a technology can enable the use of long dsRNA in mammalian cells. There is so far no reported success on introducing exogenous long dsRNA directly into the target mammalian cells due to strong cellular innate immune response, such as nonspecific interferon (IFN) responses. (Yang, S. et al. *Mol. Cell. Biol.* 21: 7807-7816 (2001)).

SUMMARY OF THE INVENTION

The present invention, in one embodiment, provides a solution to the above problem by employing a bacteria-mediated system. Bacteria do not respond to long dsRNA with innate immune response, and can function as a "shield" so that strong innate immune response of mammalian cells to long dsRNA is prevented or mitigated. According to the present invention, bacteria serve as an intermediary to solve the incompatibility between long dsRNA and mammalian cells by performing the task of producing, processing and presenting processed long dsRNA and its products to a target mammalian cell, e.g., a mammalian or other eukaryotic cell, thereby bypassing strong innate immune response. To accomplish this, bacteria with cell-invasive properties are transformed with vectors that each encodes a long dsRNA that includes a sequence that is substantially complementary to a messenger RNA (mRNA) sequence of a target eukaryotic or viral gene. In one embodiment, the dsRNA is non-coding, or non-protein-coding. When these bacteria containing long dsRNAs and their metabolic products invade a host cell, such cocktail of RNA duplexes are shielded away from recognition by immune sensors on the cell surface. When bacteria eventually release the expressed RNAs into the cytoplasma of mammalian cells, likely some or all of the expressed long dsRNA has been processed by bacterial and mammalian Dicer and/or Dicer-like enzymes into a cocktail of short RNA duplexes. Because of its great variety that covers almost all motifs of an mRNA, some of the bacterial content, which may have been further processed by mammalian enzymes and organelles, will turn out to function as gene silencing RNAs that generate varying degrees of gene silencing effects. Thus, the expression of the target eukaryotic or viral gene is effectively reduced. In one embodiment, the gene silencing can be attributed to a mixture of short RNA duplexes that result from the bacterial transfection, but the present invention should not be construed to be limited to such interpretation.

Because methods of the present invention do not require screening for an effective siRNA motif against a particular gene within an mRNA, and enables simultaneous synthesis and delivery, the present invention has dramatically simplified and advanced gene targeting by RNAi in gene function research and gene-targeting therapy where bacteria can be applied. For example, to use synthetic siRNAs to trigger RNAi, each mRNA for a target gene must be screened for an efficient siRNA, a trials-and-errors process. For some genes, identifying an efficacious siRNA motif has been unachievable. In contrast, the present invention relies on a long dsRNA, which, in one embodiment, results in a mixture of short RNA duplexes, in order to effect sequence-specific gene silencing, thereby bypassing the pre-screening process.

Because the metabolic products from the bacteria-produced long dsRNA cover almost all motifs of an mRNA, the present invention also guards against disease genes that mutate frequently, as in the case of some viral genes like HIV. After an effective siRNA is designed and developed, a mutation can take place in the targeted motif of the gene that can render the siRNA completely ineffective. In contrast, the bacteria-mediated gene-targeting using long dsRNA can circumvent such an issue since numerous motifs of the disease or viral gene are targeted by the processed long dsRNA.

The present invention also provides a powerful tool for target identification and validation and this tool is referred to as Therapeutic Pathway Identification and Validation (TPIV®) technology. As an example, the present invention enables a genome-wide approach to target discovery by providing a TPIV® library that would otherwise be impossible to construct. The present invention also provides enabling technology for gene-targeting in vivo to discover, validate and prioritize therapeutic targets. The RNAi effects from methods of the present invention turn out to be more potent and specific than currently-available RNAi technologies. For instance, methods according to the present invention were able to effect gene silencing in cancer stem cells which are notoriously difficult to manipulate genetically.

Accordingly, in general, the present invention provides systems, materials and methods related to the following: a bacterium is genetically engineered to transcribe a non-small-hairpin RNA (or non-short-hairpin RNA, both abbreviated as "non-shRNA"). This non-shRNA can be a long double-strand RNA (dsRNA), a long hairpin RNA (lhRNA), or a polycistronic shRNA, or a mixture of any of the above. The non-shRNA can be non-coding, or non-protein-coding. The non-shRNA is processed, in one embodiment, to a mixture of shorter RNA duplexes, in the bacterium before being presented to a target eukaryotic cell. In one feature, bacteria with invasive property are selected to carry out the present invention. The metabolic products from the bacteria are capable of modulating gene expression in the target cell.

In one aspect, the present invention provides a prokaryotic vector that encodes a long, double-strand RNA (dsRNA) or lhRNA under the control of one or more prokaryotic promoters. The dsRNA includes a sequence substantially complementary (including being perfectly complementary) to a messenger RNA (mRNA) sequence of a target eukaryotic gene or viral gene. In one embodiment, prokaryotic metabolites of the dsRNA are capable of modulating the expression of the eukaryotic gene or viral gene. In one embodiment, the vector includes at least two prokaryotic promoters which can be the same (e.g., T7). Each promoter controls the expression of one or the other of the two substantially complementary strands of said dsRNA. In one embodiment, the vector is a circular, double-strand plasmid, and the two prokaryotic promoters are disposed on complementary strands of the plasmid. In another embodiment, the vector can be integrated into a bacterial chromosome. In yet another embodiment, the vector an exist as an episome in bacteria. The eukaryotic gene whose expression is targeted by the vector can be a cancer gene or an HIV gene, for example.

In another aspect, the present invention provides a bacterium comprising (a) a RNA molecule with a double-strand region, e.g., a long, double-strand RNA (dsRNA) or a lhRNA, or (b) a DNA molecule encoding the RNA. A single DNA molecule may consist of two complementary strands, each encoding for one corresponding RNA strand. The RNA includes a sequence substantially complementary to an mRNA sequence of a target eukaryotic gene or viral gene. The double-strand region of the RNA, in one feature, is at least 40 bp, 70 bp, 100 bp, 200 bp, 400 bp, or 1000 bp in length, and, in another feature, no more than 2000 bp in length. In one embodiment, the bacterium can be invasive, non-pathogenic, and/or therapeutic. In one embodiment, the bacterium is capable of processing the RNA into a mixture of shorter RNA duplexes that are capable of modulating expression of the target gene. To do that, the bacterium may also contain an enzyme or ribozyme capable of processing the RNA into a mixture of shorter RNA duplexes, e.g., one or more endonucleases, such as a bacterial RNase III or a Dicer or both. In an embodiment, the bacterium contains an enzyme that assists in transporting genetic materials, upon their release from the bacterium, into the cytoplasm of a target eukaryotic cell. That enzyme can be an Hly protein (e.g., listeriolysin O as encoded by the Hly A gene). The same DNA molecule encoding the RNA or a different DNA can encode the Hly gene. In another embodiment, the bacterium is capable of modulating the expression of the eukaryotic gene or viral gene in a eukaryotic cell after being introduced into a eukaryotic cell, i.e., not necessarily through the path of the mixture of short RNA duplexes. One embodiment of the RNA-encoding DNA molecule is the vector described immediately above.

In another aspect, the present invention provides a bacterium comprising a mixture of short RNA duplexes that is capable of modulating the expression of a eukaryotic gene or viral gene. The mixture of short RNA duplexes can be produced from a non-small-hairpin RNA (non-shRNA). In one embodiment, the mixture of short RNA duplexes is capable of effectively reducing the expression of a eukaryotic or viral gene. The non-shRNA can be a long double-strand RNA, a long hairpin RNA, or a polycistronic shRNA.

In another aspect, the present invention provides a library called a TPIV® library that comprises a plurality of vectors, each vector comprising one cDNA molecule from a cDNA pool or one cDNA fragment, a first promoter, and a second promoter. The first promoter controls the expression of one strand of the cDNA molecule or of the cDNA fragment, and the second promoter controls the expression of the other strand of the cDNA molecule or of the cDNA fragment. And the plurality of vectors can transform bacteria. The cDNA pool may be derived from total mRNA from mammalian cells. In one embodiment, the cDNA fragment is produced by digesting a cDNA molecule with a restriction enzyme or through a PCR reaction. An inventive aspect of the present invention is also directed to one or more vectors found in such a library.

The present invention also provides another embodiment of the TPIV® library that comprises bacterial cells that contain a plurality of vectors described above. In one embodiment, the transcripts of the cDNA molecule or cDNA fragment can form a long dsRNA. In one embodiment, the double-strand RNA transcribed from the two strands of the cDNA molecule or cDNA fragment is processed into a mixture of shorter RNA duplexes. An inventive aspect of the present invention is also directed to one or more bacteria found in such a library.

In a further aspect, the present invention also provides various methods of using the vectors, bacteria, and libraries of the invention for therapeutic and research uses. For instance, in one aspect, a method is provided for identifying a therapeutic target, the method comprising infecting a population of cells with the library of the present invention and selecting a cell with a phenotypic change to identify a therapeutic target.

In one aspect, the present invention provides a method of investigating a pathway component in vitro, the method comprising: providing a eukaryotic cell capable of carrying out a biological pathway of interest; infecting the cell with the bacterium of the present invention whose target eukaryotic gene or viral gene is suspected to be a component of the pathway of interest; and subsequently analyzing said cell for any effect on said pathway of interest. In one embodiment, the long dsRNA expressed in the bacteria and its products in the bacteria interfere with the mRNA of the suspect component, thereby regulating the pathway. In one embodiment, the pathway affects cell survival, growth, differentiation, aging, autophage, division, or death. In another embodiment, the target affects the survival, proliferation and pathogenicity of an infectious organism, such as virus. The eukaryotic cell can be an animal cell, a stem cell, a cancer cell, and so on. In one embodiment, the cell is a cancer stem cell.

In one aspect, the present invention provides a method of investigating a therapeutic target in vivo, the method comprising: providing a live animal having cells that exhibit a disorder; delivering the bacterium of the present invention to those animal cells for bactofection; and subsequently harvesting infected cells to check for therapeutic effect. The animal cells can comprise a xenograft and/or tumor cells.

In one aspect, the present invention provides a method of introducing a mixture of short RNA duplexes into an animal cell, the method comprising producing, processing and presenting at least one long double-strand RNA (dsRNA) to an animal cell without triggering significant immune response from the animal. The dsRNA can be processed into the mixture of shorter RNA duplexes. In one embodiment, the method comprises producing and processing said dsRNA inside a bacterium, infecting the animal cell with the bacterium, and lysing the bacterium to release its content. According to the method, the content of the bacterium may be further processed in the animal cell to become the mixture of short RNA duplexes.

The present invention also provides a method of regulating gene expression in a target eukaryotic cell, which can be a mammalian, avian, or other eukaryotic cell. The method comprises infecting the target cell with the bacterium of the present invention, wherein eukaryotic gene or viral gene targeted by the bacterium is the gene to be regulated.

The present invention further provides a method of treating or preventing cancer or a cell proliferation disorder in a subject, the method comprising infecting the cells of the subject with the bacterium of the invention, wherein the eukaryotic gene or viral gene targeted by the bacterium is a gene known to up-regulate cell proliferation. In an embodiment, the subject is mammalian, avian, or other kind of eukaryotic organism.

The present invention further provides a method of treating or preventing diseases in a subject caused by viral infection. The method includes the step of infecting the cells of the subject with the bacterium of the invention, where the eukaryotic gene or viral gene targeted by the bacterium is implicated in the pathogenicity of the virus.

The present invention further provides a method of treating or preventing diseases in a subject caused by an altered gene, the method comprising infecting the cells of the subject with the bacterium of the invention, wherein the eukaryotic gene or viral gene targeted by the bacterium is the altered gene. In one embodiment, the disease is caused, at least in part, by the upregulation or downregulation of that gene's expression. In anther embodiment, the disease is caused, at least in part, by one or more mutations in the gene.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention without departing from the principles of the present invention. All embodiments can be used in conjunction with each other.

DETAILED DESCRIPTION OF THE INVENTION

Figure 1:
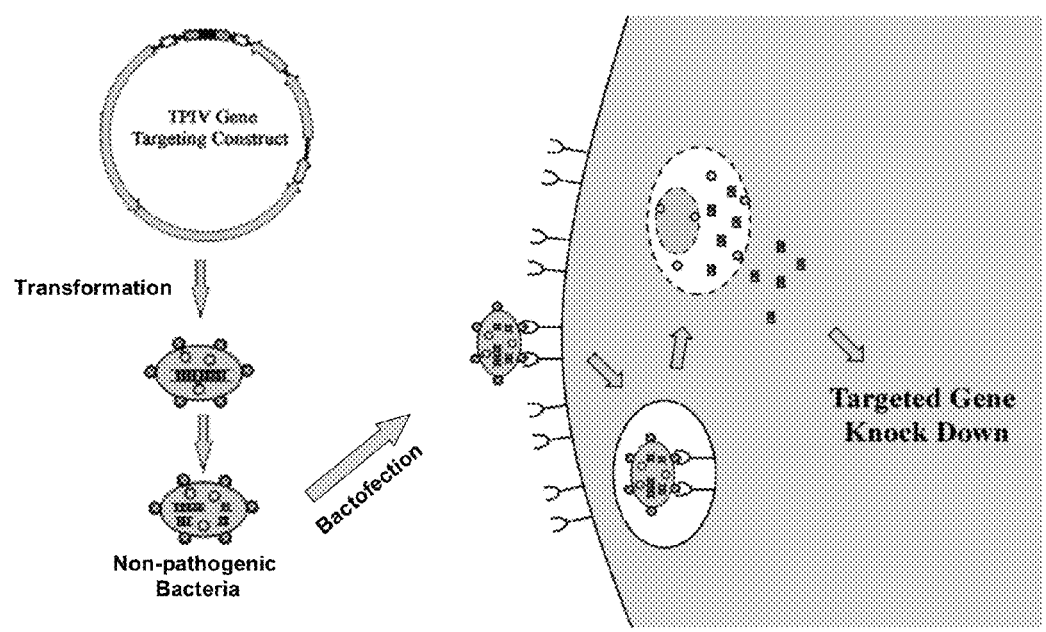
FIG. 1 is a schematic diagram of an embodiment of the present invention.

As used herein, "modulating" refers to either increasing or decreasing (e.g., silencing), in other words, either upregulating or downregulating. As used herein, "introducing" or "delivering" a microorganism to a target cell, refers to the process of infecting the target cell with the microorganism (e.g., a bacterium), and, in certain cases, releasing the genetic materials inside the microorganism into a desired location of the target cell (e.g., the cytoplasm), possibly through lysing the microorganism.

The present invention provides a platform technology for target discovery and gene-silencing therapy. In one aspect, the present system produces and delivers DNA encoding long dsRNA or long dsRNA, or both to mammalian cells or other types of eukaryotic cells using invasive bacteria, to effect RNA interference (RNAi) in eukaryotic cells. The RNA of the present invention is non-small-hairpin RNA (non-shRNA). In one embodiment, the RNA is non-coding. "Non-coding" or "non-protein-coding" as used herein means the sequence is not to be translated into protein. In an embodiment, the non-small-hairpin RNA is long double strand RNA (dsRNA), long hairpin RNA (lhRNA), or polycistronic shRNA (Kim & Rossi, *Nature Rev. Genet.* 8:173-184 (2007)). In a preferred embodiment, the non-shRNA is a non-coding long dsRNA that can be digested or otherwise processed into shorter fragments in a bacterial cell. In one mechanism, the long dsRNA is processed into a mixture of shorter RNA duplexes. Genetic materials processed from the long dsRNA by the bacteria can be introduced into an animal host without being detected by the host cell's immune system, and proceed to modulate gene expressions in host cells via effective post-transcriptional silencing and other mechanisms. The eukaryotic cells can be mammalian, avian cells or other eukaryotic cells. The gene of interest can be a mammalian, avian, bacterial, eukaryotic, or viral gene.

By leveraging a novel gene silencing technology, the present invention provides a powerful tool for analyzing gene function both in vitro and in vivo; this tool is referred to as Therapeutic Pathway Identification and Validation (TPIV®) technology.

In one feature, the present invention provides a research tool (TPIV®) for in vitro target discovery and validation. This aspect of the invention finds application in any cell populations including cancer stem cells (CSCs) or other cell populations with unknown or not-yet-fully-defined biological pathways including non-cancer stem cells. Because the present invention is able to effect gene-silencing in CSCs, its proven potency is particularly advantageous for utilization in minute cell populations, non-culturable cell populations or those not amenable to traditional genetic manipulation.

In another feature, the present invention provides in vivo gene knockdown technology that efficiently identifies, validates, and/or prioritizes therapeutic targets. The present invention can be applied to any in vivo disease models where bacteria can be administered, yet current knockout technology cannot be used in any established disease model.

In yet another feature, the present invention also enables a genome-wide approach to target discovery. RNAi libraries constructed using the TPIV® technology can be genome wide or of a gene family. Compared to current synthetic siRNA libraries and RNAi vector libraries, the TPIV® libraries are less labor-intensive less expensive. Further, TPIV® libraries enable discovery of new genes while those others libraries do not. Therefore, the present invention provides a powerful tool for systematically probing gene function on a whole genome scale and also a powerful method for screening for potential therapeutic targets associated with diseases.

In one advantageous aspect, the present invention provides a method of producing and presenting metabolic products of a non-shRNA that, in some cases, are a mixture of short RNA duplexes, to eukaryotic cells using bacteria, preferably non-pathogenic or therapeutic strains of bacteria, to effect RNA interference (RNAi) in eukaryotic cells. The non-shRNA can be a long double strand RNA (dsRNA), long hairpin RNA (lhRNA), or polycistronic shRNA. The non-shRNAs have a region of double-strand RNA. The double-strand region is longer than siRNA duplexes, which are typically 20-25 bp. In one embodiment, the double-strand region is at least 40 bp, 70 bp, 100 bp, 200 bp, 400 bp, 1000 bp in length, and, in another feature, no more than 2000 bp in length.

As used herein, "a mixture of," "a variety of", or "a cocktail of" indicates at least two articles of different sequences. For example, in an embodiment, a mixture of short RNA duplexes comprises more than 2, 4, 8, 16, 32, 50, 100, 200, 500, 1000, 2000, or 4000 short RNA duplexes that are different from each other in sequence. In contrast, "a plurality of" indicates more than one article, whether they are of the same sequence or not.

In an embodiment, the short RNA duplexes are produced from the digestion of a non-shRNA precursor by an enzyme or ribozyme. The enzyme can be an endonuclease. The endonuclease can be a member of RNase III family, such as a bacterial RNase III or a Dicer, or a Dicer-like enzyme.

In a preferred embodiment, the non-shRNA is a long double strand RNA (dsRNA), or a long hairpin RNA (lhRNA). In an embodiment, the non-shRNA comprises a sequence substantially complementary to an mRNA sequence of a gene of interest in the target eukaryotic cells. To be substantially complementary, the two sequences do not have to have the same or similar length, and 100 percent or perfect complementarity is one example of substantial complementarity. In an embodiment, the non-shRNA precursor comprises an effective RNAi sequence against the gene of interest. In a particular example, that effective RNAi sequence is an siRNA sequence, but this may not always be the case. Not every siRNA complementary to the target gene is effective in triggering RNAi to degrade the transcripts of the gene. Indeed, time-consuming screening is usually necessary to identify an effective siRNA sequence. A genetic material that comprises "an effective RNAi (or, in one embodiment, siRNA) sequence of a gene" or that can "effectively silence a gene" is capable of substantially reducing the expression of the gene by at least 20%, 40%, 50%, 60%, 70%, 80%, 90% or more than 90%, e.g., to result in an observable phenotypic change.

The present invention also provides bacteria, preferably non-pathogenic or therapeutic bacteria, for "shielding" or producing and processing the non-shRNA into effective gene silencing products to evade higher organism's immune system. The bacterium of the invention comprises (a) a non-shRNA, (b) DNA encoding the non-shRNA, or (c) both. In an embodiment, the precursor comprises a non-encoding, long dsRNA. The bacteria can further comprise an enzyme or ribozyme that is capable of processing the precursor into siRNAs. The enzyme can be an endonuclease such as bacterial RNase III or Dicer. In one embodiment, the enzyme is endogenous to the bacterium. In another embodiment, the enzyme is exogenous to the bacterium and is introduced through vectors that express the enzyme, e.g., a dicer-like enzyme.

Bacterial delivery is more attractive than viral delivery as it can be controlled by use of antibiotics and attenuated bacterial strains which are unable to multiply. Also, bacteria are much more accessible to genetic manipulation which allows the production of vector strains specifically tailored to certain applications. In one embodiment of the invention, the methods of the present invention are used to create bacteria that cause gene-targeting in a tissue specific manner.

The non-virulent bacteria of the present invention may enter a mammalian host cell through various mechanisms. In contrast to uptake of bacteria by professional phagocytes, which normally results in the destruction of the bacterium within a specialized lysosome, invasive bacteria strains have the ability to invade non-phagocytic host cells. Naturally occurring examples of such bacteria are intracellular pathogens such as *Listeria, Shigella* and *Salmonella*, but this property can also be transferred to other bacteria such as *E. coli* and Bifidobacteriae, including probiotics through transfer of invasion-related genes (P. Courvalin, S. Goussard, C. Grillot-Courvalin, *C. R. Acad. Sci.* Paris 318, 1207 (1995)). In other embodiments of the invention, bacteria used to deliver interfering RNAs to host cells include *Shigella flexneri* (D. R. Sizemore, A. A. Branstrom, J. C. Sadoff, Science 270, 299 (1995)), invasive *E. coli* (P. Courvalin, S. Goussard, C. Grillot-Courvalin, *C. R. Acad. Sci. Paris* 318, 1207 (1995), C. Grillot-Courvalin, S. Goussard, F. Huetz, D. M. Ojcius, P. Courvalin, *Nat Biotechnol* 16, 862 (1998)), *Yersinia enterocolitica* (A. Al-Mariri A, A. Tibor, P. Lestrate, P. Mertens, X. De Bolle, J. J. Letesson *Infect Immim* 70, 1915 (2002)) and *Listeria monocytogenes* (M. Hense, E. Domann, S. Krusch, P. Wachholz, K. E. Dittmar, M. Rohde, J. Wehland, T. Chakraborty, S. Weiss, *Cell Microbiol* 3, 599 (2001), S. Pilgrim, J. Stritzker, C. Schoen, A. Kolb-Maurer, G. Geginat, M. I Loessner, I. Gentschev, W. Goebel, *Gene Therapy* 10, 2036 (2003)). Any invasive bacterium is useful for DNA transfer into eukaryotic cells (S. Weiss, T. Chakraborty, *Curr Opinion Biotechnol* 12, 467 (2001)).

Referring to FIG. 1, in an embodiment of the present invention, a mixture of various short RNA duplexes is produced in the invasive and preferably non-pathogenic bacteria and then taken up by the target eukaryotic cells. First, a prokaryotic vector, e.g., a plasmid, that encodes a non-shRNA comprising a sequence substantially complementary to a target gene's mRNA sequence is constructed and transformed into a bacterium. The expression of the non-shRNA is controlled by one or more prokaryotic promoters (e.g. T7). The plasmid illustrated in FIG. 1, has two prokaryotic promoters. In an embodiment where the non-shRNA is a long dsRNA, each promoter controls the expression of one of the complementary strand of the dsRNA. An exemplary plasmid will be described in further detail in the Example section and in reference to FIG. 3. Once the non-shRNA precursor is transcribed in the bacterium, it is then digested by endogenous bacterial RNase III, or exogenous dicer-like enzymes, into a variety of fragments, e.g., short RNA duplexes. Of course, at any given time, the bacterium may contain a mixture of non-shRNA, digested fragments (e.g. short RNA duplexes) and RNA-encoding DNAs.

Still referring to FIG. 1, during bacterial invasion ("bactofection"), the bacterium is taken up by a target eukaryotic, for example, via endosome. Bacterial content including the digested products of the non-shRNA (e.g., short RNA duplexes) is liberated within the cell's cytoplasm via after bacterial lysis, resulting in targeted gene knock down or silencing. The bacterial RNase III may be replaced by Dicer by expressing a Dicer gene and deleting RNase III gene in the bacteria. Dicer has been reported to use what is termed "ruler mechanism" to cleave a long dsRNA into shorter fragments between 12-30 nucleotides.

Alternatively, after non-shRNA precursor and its bacterially digested products have been introduced to the eukaryotic cell, they can be further processed and digested by eukaryotic enzymes including Dicer in the eukaryotic cells. This may contribute to effective RNAi by the metabolic products from non-shRNAs.

Liberation of bacterial DNAs and RNAs from the intracellular bacteria may occur through various mechanisms depending on bacterial strains. In one embodiment, the bacterial DNAs and RNAs may comprise a mixture of long dsRNAs, short RNA duplexes, and/or dsRNA-encoding plasmids. One mechanism involves the type III export system in *S. typhimurium*, a specialized multiprotein complex spanning the bacterial cell membrane whose functions include secretion of virulence factors to the outside of the cell to allow signaling towards the target cell, but which can also be used to deliver antigens into target cells. (Riissmann H. *Int J Med Microbiol*, 293:107-12 (2003)) or through bacterial lysis and liberation of bacterial contents into the cytoplasm. The lysis of intracellular bacteria is triggered through addition of an intracellularly active antibiotic (tetracycline) or occurs naturally through bacterial metabolic attenuation (auxotrophy) or through cellular endosome or lysosome. After liberation of the eukaryotic transcription plasmid, dsRNAs or siRNAs are produced within the target cell and, in turn, trigger the highly specific process of mRNA degradation, which results in silencing of the targeted gene.

The present invention can be performed using the naturally invasive pathogen *Salmonella typhimurium*. In one aspect of this embodiment, the strains of *Salmonella typhimurium* include SL 7207 and VNP20009 (S. K. Hoiseth, B. A. D. Stacker, *Nature* 291, 238 (1981); Pawelek J M, Low K B, Bermudes D. *Cancer Res.* 57(20):4537-44 (Oct. 15, 1997)).

In another embodiment of the invention, the present invention is performed using attenuated *E. coli*. In one example of this embodiment, the strain of *E. coli* is BM 2710 (C. Grillot-Courvalin, S. Goussard, F. Huetz, D. M. Ojcius, P. Courvalin, Nat Biotechnol 16, 862 (1998)). In one feature of this embodiment, the BM 2710 strain is engineered to possess cell-invading properties through an invasion plasmid, e.g., one that encodes the Inv gene. According to another feature of the present invention, the bacterium of the invention contains a vector that has the Hly (listeria lysine O) gene, as the Hly protein is considered important for genetic materials escape from the entry vesicles. Obviously, that vector could be the same invasion plasmid. Accordingly, in one embodiment, the bacterium has a plasmid that encodes both the Inv and Hly genes. In one aspect of the invention, this plasmid is pGB2inv-hly. In one example, the *E. coli* strain used in the present invention is BL21 (DE3) pLysE.

The present invention also encompasses a prokaryotic vector or plasmid encoding a non-shRNA precursor for use with invasive bacteria to effect RNA interference (RNAi) in eukaryotic cells. In one feature, the plasmid also includes at least one prokaryotic promoter that controls the expression of the non-shRNA, e.g., a non-coding, long dsRNA.

The present invention also provides a method of introducing a mixture of short RNA duplexes into eukaryotic cells using bacteria, preferably non-pathogenic or therapeutic strains of bacteria, to effect RNA interference (RNAi) in eukaryotic cells. This method can be used to modulate or regulate gene expression inside target cells via effective post-transcriptional silencing. The eukaryotic cells can be mammalian cells or avian cells. The gene of interest can be can be a mammalian, avian, bacterial, eukaryotic, or viral gene.

The present invention has wide range of applications as a research tool for identifying and validating pathway components and therapeutic targets, both in vitro and in vivo. The invention can be used on all types of cells including cells that are hard to study such cancer stem cells (CSCs). The present system can also be used to generate RNAi libraries as a means for genome-wide or gene-family-specific target discovery.

The present invention can also be used to develop therapeutics and drugs. Disease and disorders that can be treated by method of the present invention include cancer, cell proliferation disorder, viral infection, disease caused by gene mutation, and so on.

1. RNA Interference

RNA interference (abbreviated as RNAi) is a cellular process for the targeted destruction of single-stranded RNA (ssRNA) induced by double-stranded RNA (dsRNA). The ssRNA is gene transcript such as a messenger RNA (mRNA). RNAi is a form of (mostly) post-transcriptional gene silencing in which the dsRNA can specifically interfere with the expression of genes with sequences that are complementary to the dsRNA. The antisense RNA strand of the dsRNA targets a complementary gene transcript such as a messenger RNA (mRNA) for cleavage by a ribonuclease in a RNA-induced-silencing-complex (RISC), which is a ribonuclease-containing multi-protein complex.

RNAi has been shown to be a common cellular process in many eukaryotes. RISC, as well as Dicer, is conserved across the eukaryotic domain. RNAi is believed to play a role in the immune response to virus and other foreign genetic material.

Double-stranded RNA (or dsRNA) is RNA with two complementary strands. dsRNA forms the genetic material of some viruses. In non-mammalian cells, long dsRNA acts as a trigger to initiate the process of RNA interference, and in mammalian cells, shorter RNA duplexes must be used to avoid non-specific innate immune response. In an embodiment of the present invention, the non-shRNA has a double-strand region of at least 40 bp. In another embodiment, the long dsRNA of the present invention is equal or longer than 30 bp, 40 bp, 45 bp, 50 bp, 70 bp, 100 bp, 200 bp, 300 bp, 400 bp, 500 bp, 600 bp, 700 bp, 1000 bp, or 2000 bp. In an embodiment, the long dsRNA is no longer than 600 bp, 800 bp, 1500 bp or 2000 bp. In an embodiment, the dsRNA of the present invention does not contain any mismatch or bulge. In another embodiment, the dsRNA of the present invention contains mismatch and/or bulge.

Small interfering RNAs (siRNAs) are a class of short double-stranded RNA (dsRNA) molecules that play a variety of roles in biology. Most notably, it is involved in the RNA interference (RNAi) pathway where the siRNA interferes with the expression of a specific gene. In addition, siRNAs also play roles in the processes such as an antiviral mechanism or shaping the chromatin structure of a genome. siRNA has a relatively short double-strand RNA (dsRNA) region with 2-3 nucleotide overhangs with 5'-phosphate and 3'-hydroxyl termini. As used herein, siRNA is about 20-25 nucleotide long. Some of the short RNA duplexes produced from non-shRNAs (e.g., long dsRNA) may be siRNAs.

Hairpin RNA (hRNA) is a single-stranded RNA molecule that contains a stem formed by two complimentary sequences, and a loop sequence between the complimentary fragments. Due to the complementarity of the sense and antisense fragments, such a RNA molecule tends to be in hairpin-shaped form with a single-stranded RNA (loop) region and a double-stranded RNA (dsRNA) region. (See, e.g., Svoboda & Di Cara, *Cell. Mol. Life. Sci.* 63:901-918 (2006))

As used herein, short hairpin RNA (shRNA) is a hairpin RNA with a length of 50 nt or less. The shRNA can be processed by dicer into siRNA which then get incorporated into the siRNA induced silencing complex (RISC).

As used herein, long hairpin RNA (lhRNA) is the hairpin RNA with a length of more than 60 nt. The lhRNA can be processed by dicer into a variety of shorter RNA duplexes which may include siRNAs. In an embodiment, the length of the lhRNA is equal or longer than 70 nt, 80 nt, 100 nt, 150 nt, 200 nt, 400 nt, 700 nt, 1000 nt, 1500 nt, 2000, 4000, or 8000 nt. In an alternative embodiment, the dsRNA region of the lhRNA is equal or longer than 25 bp, 30 bp, 40 bp, 50 bp, 70 bp, 100 bp, 200 bp, 300 bp, 500 bp, 600 bp, 700 bp, 1000 bp, 2000 bp, or 4000 bp. In an embodiment, the dsRNA region of the lhRNA of the present invention does not contain any mismatch or bulge. In another embodiment, the dsRNA region of the lhRNA of the present invention contains mismatch and/or bulge. (ibid.)

Dicer is a member of RNAse III ribonuclease family. Dicer cleaves long double-stranded RNA (dsRNA), pre-microRNA (miRNA) and other short hairpin RNA (shRNA) into short double-stranded RNA fragments including siRNA. Dicer catalyzes the first step in the RNA interference pathway and initiates formation of the RNA-induced silencing complex (RISC), whose catalytic component argonaute is an endonuclease capable of degrading messenger RNA (mRNA) whose sequence is complementary to that of the siRNA guide strand.

RNase III is also found in bacteria. Bacterial RNase III cleaves long double-stranded RNA (dsRNA) into siRNA about 12-30 nucleotides long with termini identical to those produced by Dicer. The siRNAs produced with bacterial Rnase III, when delivered into animal cells, can also initiate formation of the RNA-induced silencing complex (RISC), and trigger RNAi. (Wang & Bechhofer, *J Bacteriol.* 179: 7379-7385 (1997); C. Conrad, "RNase III: a short introduction" published online at www.uni-giessen.de/~gf1265/GROUPS/KLUG/klug1_2.html).

The present invention provides digestion products, e.g., a mixture (or "variety," "cocktail") of short RNA duplexes, from the Dicer/RNase III digestion of a long dsRNA comprising a sequence substantially complementary to a target messenger RNA (mRNA) sequence. The mixture of short RNA duplexes is at least as efficacious in triggering RNAi as using a single kind of siRNA molecules with an effective siRNA sequence. The present invention thereby, in one aspect, advantageously eliminates the need for the time-consuming screening that is usually necessary for identifying an effective siRNA sequence and eliminates the delivery challenge of siRNAs.

2. Bacteria Producing, Processing and Delivering RNA or RNA-Encoding DNA to Eukaryotic Cells In the present invention, bacteria are not a simple delivery tool. Rather the bacteria perform synthesis, processing, and delivering gene-targeting RNAs. Any microorganism which is capable of synthesizing and delivering a molecule, e.g., an RNA molecule, into the cytoplasm of a target cell, such as by traversing the membrane and entering the cytoplasm of a cell, can be used to deliver RNA to such cells. In a preferred embodiment, the microorganism is a prokaryote. In an even more preferred embodiment, the prokaryote is a bacterium. Also within the scope of the present invention are microorganisms other than bacteria which can be used for delivering RNA to a cell. For example, the microorganism can be a fungus, e.g., *Cryptococciis neoformans*, protozoan, e.g., *Trypanosoma cruzi*, *Toxoplasma gondii*, *Leishmania donovani*, and *plasmodia*.

As used herein, the term "invasive" when referring to a microorganism, e.g., a bacterium, refers to a microorganism which is capable of delivering at least one molecule, e.g., an RNA or RNA-encoding DNA molecule, to a target cell. An invasive microorganism can be a microorganism which is capable of traversing a cell membrane, thereby entering the cytoplasm of said cell, and delivering at least some of its content, e.g., RNA or RNA-encoding DNA, into the target cell. The process of delivery of the at least one molecule into the target cell preferably does not significantly modify the invasion apparatus. In a preferred embodiment, the microorganism is a bacterium. A preferred invasive bacterium is a bacterium which is capable of delivering at least one molecule, e.g., an RNA or RNA-encoding DNA molecule, to a target cells, such as by entering the cytoplasm of a eukaryotic cell. Preferred invasive bacteria are live bacteria, e.g., live invasive bacteria. Invasive microorganisms include microorganisms that are naturally capable of delivering at least one molecule to a target cell, such as by traversing the cell membrane, e.g., a eukaryotic cell membrane, and entering the cytoplasm, as well as microorganisms which are not naturally invasive and which have been modified, e.g., genetically modified, to be invasive. In another preferred embodiment, a microorganism which is not naturally invasive can be modified to become invasive by linking the bacterium to an "invasion factor", also termed "entry factor" or "cytoplasm-targeting factor". As used herein, an "invasion factor" is a factor, e.g., a protein or a group of proteins which, when expressed by a non-invasive bacterium, render the bacterium invasive. As used herein, an "invasion factor" is encoded by a "cytoplasm-targeting gene". Naturally invasive microorganisms, e.g., bacteria, may have a certain tropism, i.e., preferred target cells. Alternatively, microorganisms, e.g., bacteria can be modified, e.g., genetically, to mimic the tropism of a second microorganism.

Delivery of at least one molecule into a target cell can be determined according to methods known in the art. For example, the presence of the molecule, by the decrease in expression of an RNA or protein silenced thereby, can be detected by hybridization or PCR methods, or by immunological methods which may include the use of an antibody. Determining whether a microorganism is sufficiently invasive for use in the present invention may include determining whether sufficient RNA, was delivered to host cells, relative to the number of microorganisms contacted with the host cells. If the amount of RNA, is low relative to the number of microorganisms used, it may be desirable to further modify the microorganism to increase its invasive potential.

Bacterial entry into cells can be measured by various methods. Intracellular bacteria survive treatment by aminoglycoside antibiotics, whereas extracellular bacteria are rapidly killed. A quantitative estimate of bacterial uptake can be achieved by treating cell monolayers with the antibiotic gentamicin to inactivate extracellular bacteria, then by removing said antibiotic before liberating the surviving intracellular organisms with gentle detergent and determining viable counts on standard bacteriological medium. Furthermore, bacterial entry into cells can be directly observed, e.g., by thin-section-transmission electron microscopy of cell layers or by immunofluorescent techniques (Falkow et al, (1992) Annual Rev. Cell Biol. 8:333). Thus, various techniques can be used to determine whether a specific bacteria is capable of invading a specific type of cell or to confirm bacterial invasion following modification of the bacteria, such modification of the tropism of the bacteria to mimic that of a second bacterium. Bacteria that can be used for delivering RNA according to the method of the present invention are preferably non-pathogenic. However, pathogenic bacteria can also be used, so long as their pathogenicity has been attenuated, to thereby render the bacteria non-harmful to a subject to which it is administered. As used herein, the term "attenuated bacterium" refers to a bacterium that has been modified to significantly reduce or eliminate its harmfulness to a subject. A pathogenic bacterium can be attenuated by various methods, set forth below.

Without wanting to be limited to a specific mechanism of action, the bacterium delivering the RNA into the eukaryotic cell can enter various compartments of the cell, depending on the type of bacterium. For example, the bacterium can be in a vesicle, e.g., a phagocytic vesicle. Once inside the cell, the bacterium can be destroyed or lysed and its contents delivered to the eukaryotic cell. A bacterium can also be engineered to express a phagosome degrading enzyme to allow leakage of RNA from the phagosome. In some embodiments, the bacterium can stay alive for various times in the eukaryotic cell and may continue to produce RNA. The RNA or RNA-encoding DNA can then be released from the bacterium into the cell by, e.g., leakage. In certain embodiments of the invention, the bacterium can also replicate in the eukaryotic cell. In a preferred embodiment, bacterial replication is not significantly toxic to the host cell. The present invention is not limited to delivery of RNA or RNA-encoding DNA by a specific mechanism and is intended to encompass methods and compositions permitting synthesis and/or delivery of RNA or RNA-encoding DNA by a bacterium independently of the mechanism of delivery.

Set forth below are examples of bacteria which have been described in the literature as being naturally invasive (section 2.1), as well as bacteria which have been described in the literature as being naturally non-invasive bacteria (section 2.2), as well as bacteria which are naturally non-pathogenic or which are attenuated. Although some bacteria have been described as being non-invasive (section 2.2), these may still be sufficiently invasive for use according to the invention. Whether traditionally described as naturally invasive or noninvasive, any bacterial strain can be modified to modulate, in particular to increase, its invasive characteristics (e.g., as described in section 2.3).

2.1 Naturally Invasive Bacteria

The particular naturally invasive bacteria employed in the present invention are not critical thereto. Examples of such naturally-occurring invasive bacteria include, but are not limited to, *Shigella* spp., *Salmonella* spp., *Listeria* spp., *Rickettsia* spp., and enteroinvasive *Escherichia coli*. The particular *Shigella* strain employed is not critical to the present invention.

Examples of *Shigella* strains which can be employed in the present invention include *Shigella flexneri* 2a (ATCC No. 29903), *Shigella sonnet* (ATCC No. 29930), and *Shigella disenteriae* (ATCC No. 13313). An attenuated *Shigella* strain, such as *Shigella flexneri* 2a 2457T aroA virG mutant CVD 1203 (Noriega et al. supra), *Shigella flexneri* M90T icsA mutant (Goldberg et al *Infect Immun.,* 62:5664-5668 (1994)), *Shigella flexneri* Y SFL1 14 aroD mutant (Karnell et al. *Vacc,* 10:167-174 (1992)), and *Shigella flexneri* aroA aroD mutant (Verma et al *Vacc,* 9:6-9 (1991)) are preferably employed in the present invention. Alternatively, new attenuated *Shigella* spp. strains can be constructed by introducing an attenuating mutation either singularly or in conjunction with one or more additional attenuating mutations.

At least one advantage to *Shigella* RNA vaccine vectors is their tropism for lymphoid tissue in the colonic mucosal surface. In addition, the primary site of *Shigella* replication is believed to be within dendritic cells and macrophages, which are commonly found at the basal lateral surface of M cells in mucosal lymphoid tissues (reviewed by McGhee, J. R. et al *Reproduction, Fertility,* & *Development* 6:369 (1994); Pascual, D. W. et al *Immunomethods* 5:56 (1994)). As such, *Shigella* vectors may provide a means to express antigens in these professional antigen presenting cells. Another advantage of *Shigella* vectors is that attenuated *Shigella* strains deliver nucleic acid reporter genes in vitro and in vivo (Sizemore, D. R. et al. *Science* 270:299 (1995); Courvalin, P. et al *Comptes Rendus de l Academie des Sciences Serie Ill-Sciences de Ia Vie-Life Sciences* 318:1207 (1995); Powell, R. J. et al In: Molecular approaches to the control of infectious diseases (1996). F. Brown, E. Norrby, D. Burton and J. Mekalanos, eds. Cold Spring Harbor Laboratory Press, New York. 183; Anderson, R. J. et al Abstracts for the 97th General Meeting of the American Society for Microbiology: E. (1997)). On the practical side, the tightly restricted host specificity of *Shigella* stands to prevent the spread of *Shigella* vectors into the food chain via intermediate hosts. Furthermore, attenuated strains that are highly attenuated in rodents, primates and volunteers have been developed (Anderson et al (1997) supra; Li, A. et al *Vaccine* 10:395 (1992); Li, A. et al *Vaccine* 11:180 (1993); Karnell, A. et al *Vaccine* 13:88 (1995); Sansonetti, P. J. and J. Arondel *Vaccine* 7:443 (1989); Fontaine, A. et al. *Research in Microbiology* 141:907 (1990); Sansonetti, P. J. et al. (1991) *Vaccine* 9:416; Noriega, F. R. et al. *Infection & Immunity* 62:5168 (1994); Noriega, F. R. et al. *Infection & Immunity* 64:3055 (1996); Noriega, F. R. et al. *Infection & Immunity* 64:23 (1996); Noriega, F. R. et al. *Infection & Immunity* 64:3055 (1996); Kotloff, K. L. et al. *Infection & Immunity* 64:4542 (1996)). This latter knowledge will allow the development of well tolerated *Shigella* vectors for use in humans.

Attenuating mutations can be introduced into bacterial pathogens using non-specific mutagenesis either chemically, using agents such as N-methyl-N'-nitro-N-nitrosoguanidine, or using recombinant DNA techniques; classic genetic techniques, such as Tn10 mutagenesis, P22-mediated transduction, λ phage mediated crossover, and conjugational transfer; or site-directed mutagenesis using recombinant DNA techniques. Recombinant DNA techniques are preferable since strains constructed by recombinant DNA techniques are far more defined. Examples of such attenuating mutations include, but are not limited to: (i) auxotrophic mutations, such as aro (Hoiseth et al. *Nature*, 291:238-239 (1981)), gua (McFarland et al *Microbiol. Path.*, 3:129-141 (1987)), nad (Park et al. *J Bact*, 170:3725-3730 (1988), thy (Nnalue et al. *Infect. Immun.*, 55:955-962 (1987)), and asd (Curtiss, supra) mutations;

(ii) mutations that inactivate global regulatory functions, such as cya (Curtiss et al. *Infect. Immun.*, 55:3035-3043 (1987)), crp (Curtiss et al (1987), supra), phoP/phoQ (Groisman et al. *Proc. Natl. Acad. Sci., USA*, 86:7077-7081 (1989); and Miller et al. *Proc. Natl. Acad. Sci., USA*, 86:5054-5058 (1989)), phop$^c$ (Miller et al. J. Bact, 172: 2485-2490 (1990)) or ompR (Dorman et al. *Infect. Immun.*, 57:2136-2140 (1989)) mutations;

(iii) mutations that modify the stress response, such as recA (Buchmeier et al. *Mol. Micro.*, 7:933-936 (1993)), htrA (Johnson et al. *Mol. Micro.*, 5:401-407 (1991)), htpR (Neidhardt et al. *Biochem. Biophys. Res. Corn.*, 100:894-900 (1981)), hsp (Neidhardt et al. *Ann. Rev. Genet*, 18:295-329 (1984)) and groEL (Buchmeier et al. *Sci.*, 248:730-732 (1990)) mutations;

(iv) mutations in specific virulence factors, such as IsyA (Libby et al. *Proc. Natl. Acad. Sci., USA*, 91:489-493 (1994)), pag or prg (Miller et al (1990), supra; and Miller et al (1989), supra), iscA or virG (d'Hauteville et al. *Mol. Micro.*, 6:833-841 (1992)), plcA (Mengaud et al. *Mol. Microbiol.*, 5:367-72 (1991); Camilli et al. *J. Exp. Med*, 173:751-754 (1991)), and act (Brundage et al. *Proc. Natl. Acad. Sci., USA*, 90:11890-11894 (1993)) mutations; (v) mutations that affect DNA topology, such as top A (Galan et al. *Infect. Immun.*, 58: 1879-1885 (1990));

(vi) mutations that disrupt or modify the cell cycle, such as min (de Boer et al. *Cell*, 56:641-649 (1989)).

(vii) introduction of a gene encoding a suicide system, such as sacB (Recorbet et al. *App. Environ. Micro.*, 59:1361-1366 (1993); Quandt et al. *Gene*, 127:15-21 (1993)), nuc (Ahrenholtz et al. *App. Environ. Micro.*, 60:3746-3751 (1994)), hok, gef, kil, or phiA (Molin et al. *Ann. Rev. Microbiol.*, 47:139-166 (1993));

(viii) mutations that alter the biogenesis of lipopolysaccharide and/or lipid A, such as rFb (Raetz in *Esherishia coli* and *Salmonella typhimurium*, Neidhardt et al, Ed., ASM Press, Washington D.C. pp 1035-1063 (1996)), galE (Hone et al. *J. Infect. Dis.*, 156:164-167 (1987)) and htrB (Raetz, supra), msbB (Reatz, supra)

(ix) introduction of a bacteriophage lysis system, such as lysogens encoded by P22 (Rennell et al. *Virol*, 143:280-289 (1985)), λ murein transglycosylase (Bienkowska-Szewczyk et al. *Mol. Gen. Genet.*, 184:111-114 (1981)) or S-gene (Reader et al. *Virol*, 43:623-628 (1971)); and The attenuating mutations can be either constitutively expressed or under the control of inducible promoters, such as the temperature sensitive heat shock family of promoters (Neidhardt et al. supra), or the anaerobically induced nirB promoter (Harborne et al. *Mol. Micro.*, 6:2805-2813 (1992)) or repressible promoters, such as uapA (Gorfinkiel et al. *J. Biol. Chem.*, 268:23376-23381 (1993)) or gcv (Stauffer et al. *J. Bact*, 176:6159-6164 (1994)).

The particular *Listeria* strain employed is not critical to the present invention. Examples of *Listeria* strains which can be employed in the present invention include *Listeria monocytogenes* (ATCC No. 15313). Attenuated *Listeria* strains, such as *L. monocytogenes* actA mutant (Brundage et al. supra) or *L. monocytogenes* picA (Camilli et al. *J. Exp. Med.*, 173:751-754 (1991)) are preferably used in the present invention. Alternatively, new attenuated *Listeria* strains can be constructed by introducing one or more attenuating mutations in groups (i) to (vii) as described for *Shigella* spp. above. The particular *Salmonella* strain employed is not critical to the present invention.

Examples of *Salmonella* strains which can be employed in the present invention include *Salmonella typhi* (ATCC No. 7251) and *S. typhimurium* (ATCC No. 13311). Attenuated *Salmonella* strains are preferably used in the present invention and include *S. typhi*-aroC-aroD (Hone et al. *Vacc.* 9:810 (1991) and *S. typhiinurium*-axoA mutant (Mastroeni et al. *Micro. Pathol.* 13:477 (1992)). Alternatively, new attenuated *Salmonella* strains can be constructed by introducing one or more attenuating mutations as described fro *Shigella* spp. above.

The particular *Rickettsia* strain employed is not critical to the present invention. Examples of *Rickettsia* strains which can be employed in the present invention include *Rickettsia Rickettsiae* (ATCC Nos. VR149 and VR891), *Riketsia prowaseckii* (ATCC No. VR233), *Rickettsia tsutsugamuchi* (ATCC Nos. VR312, VR150 and VR609), *Rickettsia mooseri* (ATCC No. VR144), *Rickettsia sibirica* (ATCC No. VR151), and *Rochalimaea quitana* (ATCC No. VR358). Attenuated *Rickettsia* strains are preferably used in the present invention and can be constructed by introducing one or more attenuating mutations in groups (i) to (vii) as described for *Shigella* spp. above.

The particular enteroinvasive *Escherichia* strain employed is not critical to the present invention. Examples of enteroinvasive *Escherichia* strains which can be employed in the present invention include *Escherichia coli* strains 4608-58, 1184-68, 53638-C-17, 13-80, and 6-81 (Sansonetti et al. *Ann. Microbiol.* (Inst. Pasteur), 132A:351-355 (1982)).

Attenuated enteroinvasive *Escherichia* strains are preferably used in the present invention and can be constructed by introducing one or more attenuating mutations in groups (i) to (vii) as described for *Shigella* spp. above.

Furthermore, since certain microorganisms other than bacteria can also interact with integrin molecules (which are receptors for certain invasion factors) for cellular uptake, such microorganisms can also be used for introducing RNA into target cells. For example, viruses, e.g., foot-and-mouth disease virus, echovirus, and adenovirus, and eukaryotic pathogens, e.g., *Histoplasma capsulatum* and *Leishmania major* interact with integrin molecules.

2.2 Less Invasive Bacteria

Examples of bacteria which can be used in the present invention and which have been described in the literature as being non-invasive or at least less invasive than the bacteria listed in the previous section (2.1) include, but are not limited to, *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., and *Erysipelothrix* spp. It may be necessary to modify these bacteria to increase their invasive potential. Bacteria can also be made in half-live state for improving safety and/or efficacy. The particular *Yersinia* strain employed is not critical to the present invention.

Examples of *Yersinia* strains which can be employed in the present invention include *Y. enterocolitica* (ATCC No. 9610) or *Y. pestis* (ATCC No. 19428). Attenuated *Yersinia* strains, such as *Y. enterocolitica* YeO3-R2 (al-Hendy et al. *Infect. Immun.*, 60:870-875 (1992)) or *Y. enterocolitica* aroA (O'Gaora et al. Micro. *Path.*, 9:105-116 (1990)) are preferably used in the present invention. Alternatively, new attenuated *Yersinia* strains can be constructed by introducing one or more attenuating mutations in groups (i) to (vii) as described for *Shigella* spp. above.

The particular *Escherichia* strain employed is not critical to the present invention. Examples of *Escherichia* strains which can be employed in the present invention include *E. coli* H10407 (Elinghorst et al *Infect. Immun.*, 60:2409-2417 (1992)), and *E. coli* EFC4, CFT325 and CPZ005 (Donnenberg et al. *J. Infect. Dis.*, 169:831-838 (1994)). Attenuated

*Escherichia* strains, such as the attenuated turkey pathogen *E. coli* 02 carAB mutant (Kwaga et al. *Infect. Immun.*, 62:3766-3772 (1994)) are preferably used in the present invention. Alternatively, new attenuated *Escherichia* strains can be constructed by introducing one or more attenuating mutations in groups (i) to (vii) as described for *Shigella* spp. above.

The particular *Klebsiella* strain employed is not critical to the present invention.

Examples of *Klebsiella* strains which can be employed in the present invention include *K. pneumoniae* (ATCC No. 13884). Attenuated *Klebsiella* strains are preferably used in the present invention, and can be constructed by introducing one or more attenuating mutations in groups (i) to (vii) as described for *Shigella* spp. above.

The particular *Bordetella* strain employed is not critical to the present invention.

Examples of *Bordetella* strains which can be employed in the present invention include *B. bronchiseptica* (ATCC No. 19395). Attenuated *Bordetella* strains are preferably used in the present invention, and can be constructed by introducing one or more attenuating mutations in groups (i) to (vii) as described for *Shigella* spp. above.

The particular *Neisseria* strain employed is not critical to the present invention. Examples of *Neisseria* strains which can be employed in the present invention include *N. meningitidis* (ATCC No. 13077) and *N. gonorrhoeae* (ATCC No. 19424). Attenuated *Neisseria* strains, such as *N. gonorrhoeae* MS11 aro mutant (Chamberlain et al. *Micro. Path.*, 15:51-63 (1993)) are preferably used in the present invention. Alternatively, new attenuated *Neisseria* strains can be constructed by introducing one or more attenuating mutations in groups (i) to (vii) as described for *Shigella* spp. above. The particular *Aeromonas* strain employed is not critical to the present invention. Examples of *Aeromonas* strains which can be employed in the present invention include *A. eucrenophila* (ATCC No. 23309). Alternatively, new attenuated *Aeromonas* strains can be constructed by introducing one or more attenuating mutations in groups (i) to (vii) as described for *Shigella* spp. above.

The particular *Franciesella* strain employed is not critical to the present invention. Examples of *Franciesella* strains which can be employed in the present invention include *F. tularensis* (ATCC No. 15482). Attenuated *Franciesella* strains are preferably used in the present invention, and can be constructed by introducing one or more attenuating mutations in groups (i) to (vii) as described for *Shigella* spp. above.

The particular *Corynebacterium* strain employed is not critical to the present invention. Examples of *Corynebacterium* strains which can be employed in the present invention include *C. pseudotuberculosis* (ATCC No. 19410). Attenuated *Corynebacterium* strains are preferably used in the present invention, and can be constructed by introducing one or more attenuating mutations in groups (i) to (vii) as described for *Shigella* spp. above.

The particular *Citrobacter* strain employed is not critical to the present invention. Examples of *Citrobacter* strains which can be employed in the present invention include *C. freundii* (ATCC No. 8090). Attenuated *Citrobacter* strains are preferably used in the present invention, and can be constructed by introducing one or more attenuating mutations in groups (i) to (vii) as described for *Shigella* spp. above.

The particular *Chlamydia* strain employed is not critical to the present invention. Examples of *Chlamydia* strains which can be employed in the present invention include *C. pneumoniae* (ATCC No. VR1310). Attenuated *Chlamydia* strains are preferably used in the present invention, and can be constructed by introducing one or more attenuating mutations in groups (i) to (vii) as described for *Shigella* spp. above.

The particular *Hemophilus* strain employed is not critical to the present invention. Examples of *Hemophilus* strains which can be employed in the present invention include *H. sornmis* (ATCC No. 43625). Attenuated *Hemophilus* strains are preferably used in the present invention, and can be constructed by introducing one or more attenuating mutations in groups (i) to (vii) as described for *Shigella* spp. above.

The particular *Brucella* strain employed is not critical to the present invention. Examples of *Brucella* strains which can be employed in the present invention include *B. abortus* (ATCC No. 23448). Attenuated *Brucella* strains are preferably used in the present invention, and can be constructed by introducing one or more attenuating mutations in groups (i) to (vii) as described for *Shigella* spp. above.

The particular *Mycobacterium* strain employed is not critical to the present invention. Examples of *Mycobacterium* strains which can be employed in the present invention include *M. intracelhilare* (ATCC No. 13950) and *M. tuberculosis* (ATCC No. 27294). Attenuated *Mycobacterium* strains are preferably used in the present invention, and can be constructed by introducing one or more attenuating mutations in groups (i) to (vii) as described for *Shigella* spp. above.

The particular *Legionella* strain employed is not critical to the present invention. Examples of *Legionella* strains which can be employed in the present invention include *L. pneumophila* (ATCC No. 33156). Attenuated *Legionella* strains, such as a *L. pneumophila* mip mutant (Ott, FEMS Micro. Rev., 14:161-176 (1994)) are preferably used in the present invention. Alternatively, new attenuated *Legionella* strains can be constructed by introducing one or more attenuating mutations in groups (i) to (vii) as described for *Shigella* spp. above.

The particular *Rhodococcus* strain employed is not critical to the present invention. Examples of *Rhodococcus* strains which can be employed in the present invention include *R. equi* (ATCC No. 6939). Attenuated *Rhodococcus* strains are preferably used in the present invention, and can be constructed by introducing one or more attenuating mutations in groups (i) to (vii) as described for *Shigella* spp. above.

The particular *Pseudomonas* strain employed is not critical to the present invention. Examples of *Pseudomonas* strains which can be employed in the present invention include *P. aeruginosa* (ATCC No. 23267). Attenuated *Pseudomonas* strains are preferably used in the present invention, and can be constructed by introducing one or more attenuating mutations in groups (i) to (vii) as described for *Shigella* spp. above.

The particular *Helicobacter* strain employed is not critical to the present invention. Examples of *Helicobacter* strains which can be employed in the present invention include *H. mustelae* (ATCC No. 43772). Attenuated *Helicobacter* strains are preferably used in the present invention, and can be constructed by introducing one or more attenuating mutations in groups (i) to (vii) as described for *Shigella* spp. above.

The particular *Salmonella* stain employed is not critical to the present invention. Examples of *Salmonella* strains which can be employed in the present invention include *Salmonella typhi* (ATCC No. 7251) and *S. typhimurium* (ATCC No. 13311). Attenuated *Salmonella* strains are preferably used in the present invention and include *S. typhi* aroC aroD (Hone et al *Vacc*, 9:810-816 (1991)) and *S. typhimurium* aroA mutant (Mastroeni et al. *Micro. Pathol*, 13:477-491 (1992))). Alternatively, new attenuated *Salmonella* strains can be constructed by introducing one or more attenuating mutations in groups (i) to (vii) as described for *Shigella* spp. above. The particular *Vibrio* strain employed is not critical to the present invention.

Examples of *Vibrio* strains which can be employed in the present invention include *Vibrio cholerae* (ATCC No. 14035) and *Vibrio cincinnatiensis* (ATCC No. 35912). Attenuated *Vibrio* strains are preferably used in the present invention and include *V. cholerae* RSI virulence mutant (Taylor et al J. Infect. Dis., 170:1518-1523 (1994)) and *V. cholerae* ctxA, ace, zot, cep mutant (Waldor et al J. Infect. Dis., 170:278-283 (1994)). Alternatively, new attenuated *Vibrio* strains can be constructed by introducing one or more attenuating mutations in groups (i) to (vii) as described for *Shigella* spp. above.

The particular *Bacillus* strain employed is not critical to the present invention. Examples of *Bacillus* strains which can be employed in the present invention include *Bacillus subtilis* (ATCC No. 6051). Attenuated *Bacillus* strains are preferably used in the present invention and include *B. anthracis* mutant pX01 (Welkos et al *Micro. Pathol*, 14:381-388 (1993)) and attenuated BCG strains (Stover et al Nat, 351:456-460 (1991)). Alternatively, new attenuated *Bacillus* strains can be constructed by introducing one or more attenuating mutations in groups (i) to (vii) as described for *Shigella* spp. above. The particular *Erysipelothrix* strain employed is not critical to the present invention.

Examples of *Erysipelothrix* strains which can be employed in the present invention include *Erysipelothrix rhusiopathiae* (ATCC No. 19414) and *Erysipelothrix tonsillarum* (ATCC No. 43339). Attenuated *Erysipelothrix* strains are preferably used in the present invention and include *E. rhusiopathiae* Kg-Ia and Kg-2 (Watarai et al. *J. Vet. Med. Sci.*, 55:595-600 (1993)) and *E. rhusiopathiae* ORVAC mutant (Markowska-Daniel et al *Int. J. Med. Microb. Virol. Parisit. Infect. Dis.*, 277:547-553 (1992)). Alternatively, new attenuated *Erysipelothrix* strains can be constructed by introducing one or more attenuating mutations in groups (i) to (vii) as described for *Shigella* spp. above.

2.3. Methods for Increasing the Invasive Properties of a Bacterial Strain

Whether organisms have been traditionally described as invasive or non-invasive, these organisms can be engineered to increase their invasive properties, e.g., by mimicking the invasive properties of *Shigella* spp., *Listeria* spp., *Rickettsia* spp., or enteroinvasive *E. coli* spp. For example, one or more genes that enable the microorganism to access the cytoplasm of a cell, e.g., a cell in the natural host of said non-invasive bacteria, can be introduced into the microorganism.

Examples of such genes referred to herein as "cytoplasm-targeting genes" include genes encoding the proteins that enable invasion by *Shigella* or the analogous invasion genes of enteroinvasive *Escherichia*, or listeriolysin 0 of *Listeria*, as such techniques are known to result in rendering a wide array of invasive bacteria capable of invading and entering the cytoplasm of animal cells (Formal et al. *Infect. Immun.*, 46:465 (1984); Bielecke et al. *Nature*, 345:175-176 (1990); Small et al. In: Microbiology—1986, pages 121-124, Levine et al. Eds., American Society for Microbiology, Washington, D.C. (1986); Zychlinsky et al. *Molec. Micro.*, 11:619-627 (1994); Gentschev et al (1995) *Infection & Immunity* 63:4202; Isberg, R. R. and S. Falkow (1985) *Nature* 317: 262; and Isberg, R. R. et al. (1987) *Cell* 50:769). Methods for transferring the above cytoplasm-targeting genes into a bacterial strain are well known in the art. Another preferred gene which can be introduced into bacteria to increase their invasive character encodes the invasin protein from *Yersinia pseudotuberculosis*, (Leong et al. *EMBO J.*, 9:1979 (1990)). Invasin can also be introduced in combination with listeriolysin, thereby further increasing the invasive character of the bacteria relative to the introduction of either of these genes. The above genes have been described for illustrative purposes; however, it will be obvious to those skilled in the art that any gene or combination of genes, from one or more sources, that participates in the delivery of a molecule, in particular an RNA or RNA-encoding DNA molecule, from a microorganism into the cytoplasm of a cell, e.g., an animal cell, will suffice. Thus, such genes are not limited to bacterial genes, and include viral genes, such as influenza virus hemagglutinin HA-2 which promotes endosmolysis (Plank et al. *J. Biol. Chem.*, 269: 12918-12924 (1994)). The above cytoplasm-targeting genes can be obtained by, e.g., PCR amplification from DNA isolated from an invasive bacterium carrying the desired cytoplasm-targeting gene. Primers for PCR can be designed from the nucleotide sequences available in the art, e.g., in the above-listed references and/or in GenBank, which is publicly available on the interne (www.ncbi.nlm.nih.gov/). The PCR primers can be designed to amplify a cytoplasm-targeting gene, a cytoplasm-targeting operon, a cluster of cytoplasm-targeting genes, or a regulon of cytoplasm-targeting genes. The PCR strategy employed will depend on the genetic organization of the cytoplasm-targeting gene or genes in the target invasive bacteria. The PCR primers are designed to contain a sequence that is homologous to DNA sequences at the beginning and end of the target DNA sequence. The cytoplasm-targeting genes can then be introduced into the target bacterial strain, e.g., by using Hfr transfer or plasmid mobilization (Miller, A Short Course in Bacterial Genetics, Cold Spring Harbor Laboratory Press, Cold Spring Harbor, N.Y. (1992); Bothwell et al. supra; and Ausubel et al. supra), bacteriophage-mediated transduction (de Boer, supra; Miller, supra; and Ausubel et al. supra), chemical transformation (Bothwell et al. supra; Ausubel et al. supra), electroporation (Bothwel et al. supra; Ausubel et al. supra; and Sambrook, Molecular Cloning: A Laboratory Manual, Cold Spring Harbor Laboratory Press, Cold Spring Harbor, N.Y.) and physical transformation techniques (Johnston et al. supra; and Bothwell, supra). The cytoplasm-targeting genes can be incorporated into lysogenic bacteriophage (de Boer et al Cell, 56:641-649 (1989)), plasmids vectors (Curtiss et al. supra) or spliced into the chromosome (Hone et al. supra) of the target strain.

In addition to genetically engineering bacteria to increase their invasive properties, as set forth above, bacteria can also be modified by linking an invasion factor to the bacteria. Accordingly, in one embodiment, a bacterium is rendered more invasive by coating the bacterium, either covalently or non-covalently, with an invasion factor, e.g., the protein invasin, invasin derivatives, or a fragment thereof sufficient for invasiveness. In fact, it has been shown that non-invasive bacterial cells coated with purified invasin from *Yersinia pseudotuberculosis* or the carboxyl-terminal 192 amino acids of invasin are able to enter mammalian cells (Leong et al. *EMBO J.* 9:1979 (1990)). Furthermore, latex beads coated with the carboxyl terminal region of invasin are efficiently internalized by mammalian cells, as are strains of *Staphylococcus aureus* coated with antibody-immobilized invasin (reviewed in Isberg and Trail van *Nhieu Ann. Rev. Genet.* 27:395 (1994)). Alternatively, a bacterium can also be coated with an antibody, variant thereof, or fragment thereof which binds specifically to a surface molecule recognized by a bacterial entry factor. For example, it has been shown that bacteria are internalized if they are coated with a monoclonal antibody directed against an integrin molecule, e.g., $\alpha 5\beta 1$, known to be the surface molecule with which the bacterial invasin protein interacts (Isberg and Tran van Nhieu, supra). Such antibodies can be prepared according to methods known in the art. The antibodies can be tested for efficacy in mediating bacterial invasiveness by, e.g., coating bacteria with the antibody, contacting the bacteria with eukaryotic cells having a surface receptor recognized by the antibody, and monitoring the presence of intracellular bacteria, according to the methods described above. Methods for linking an invasion factor to the surface of a bacterium are known in the art and include cross-linking.

3. Target Cells

The present invention provides a method for synthesizing, processing and delivering RNA to any type of target cell. As used herein, the term "target cell" refers to a cell which can be invaded by a bacterium, i.e., a cell which has the necessary surface receptor for recognition by the bacterium.

Preferred target cells are eukaryotic cells. Even more preferred target cells are animal cells. "Animal cells" are defined as nucleated, non-chloroplast containing cells derived from or present in multicellular organisms whose taxanomic position lies within the kingdom animalia. The cells may be present in the intact animal, a primary cell culture, explant culture or a transformed cell line. The particular tissue source of the cells is not critical to the present invention. The recipient animal cells employed in the present invention are not critical thereto and include cells present in or derived from all organisms within the kingdom animalia, such as those of the families mammalia, pisces, avian, reptilia.

Preferred animal cells are mammalian cells, such as humans, bovine, ovine, porcine, feline, canine, goat, equine, and primate cells. The most preferred animal cells are human cells.

In a preferred embodiment, the target cell is in a mucosal surface. Certain enteric pathogens, e.g., *E. coli, Shigella, Listeria*, and *Salmonella*, are naturally adapted for this application, as these organisms possess the ability to attach to and invade host mucosal surfaces (Kreig et al. supra). Therefore, in the present invention, such bacteria can deliver RNA molecules or RNA-encoding DNA to cells in the host mucosal compartment.

Although certain types of bacteria may have a certain tropism, i.e., preferred target cells, delivery of RNA or RNA-encoding DNA to a certain type of cell can be achieved by choosing a bacterium which has a tropism for the desired cell type or which is modified such as to be able to invade the desired cell type. Thus, e.g., a bacterium could be genetically engineered to mimic mucosal tissue tropism and invasive properties, as discussed above, to thereby allow said bacteria to invade mucosal tissue, and deliver RNA or RNA-encoding DNA to cells in those sites.

Bacteria can also be targeted to other types of cells. For example, bacteria can be targeted to erythrocytes of humans and primates by modifying bacteria to express on their surface either, or both of, the *Plasmodium vivax* reticulocyte binding proteins-1 and -2, which bind specifically to erythrocytes in humans and primates (Galinski et al. *Cell,* 69: 1213-1226 (1992)). In another embodiment, bacteria are modified to have on their surface asialoorosomucoid, which is a ligand for the asilogycoprotein receptor on hepatocytes (Wu et al. *J. Biol. Chem.,* 263:14621-14624 (1988)). In yet another embodiment, bacteria are coated with insulin-poly-L-lysine, which has been shown to target plasmid uptake to cells with an insulin receptor (Rosenkranz et al. Expt. Cell Res., 199:323-329 (1992)). Also within the scope of the present invention are bacteria modified to have on their surface p60 of *Listeria monocytogenes*, which allows for tropism for hepatocytes (Hess et al. *Infect. Immun.,* 63:2047-2053 (1995)), or a 60 kD surface protein from *Trypanosoma cruzi* which causes specific binding to the mammalian extra-cellular matrix by binding to heparin, heparin sulfate and collagen (Ortega-Barria et al. *Cell,* 67:411-421 (1991)).

Yet in another embodiment, a cell can be modified to become a target cell of a bacterium for delivery of RNA. Accordingly, a cell can be modified to express a surface antigen which is recognized by a bacterium for its entry into the cell, i.e., a receptor of an invasion factor. The cell can be modified either by introducing into the cell a nucleic acid encoding a receptor of an invasion factor, such that the surface antigen is expressed in the desired conditions. Alternatively, the cell can be coated with a receptor of an invasion factor. Receptors of invasion factors include proteins belonging to the integrin receptor superfamily. A list of the type of integrin receptors recognized by various bacteria and other microorganisms can be found, e.g., in Isberg and Iran Van Nhieu *Ann. Rev. Genet.* 27:395 (1994). Nucleotide sequences for the integrin subunits can be found, e.g., in GenBank, publicly available on the internet.

As set forth above, yet other target cells include fish, avian, and reptilian cells. Examples of bacteria which are naturally invasive for fish, avian, and reptilian cells are set forth below.

Examples of bacteria which can naturally access the cytoplasm of fish cells include, but are not limited to *Aeromonas salminocida* (ATCC No. 33658) and *Aeromonas schuberii* (ATCC No. 43700). Attenuated bacteria are preferably used in the invention, and include *A. salmonicidia* vapA (Gustafson et al. *J. Mol. Biol.*, 237:452-463 (1994)) or *A. salmonicidia* aromatic-dependent mutant (Vaughan et al. *Infect. Immun.*, 61:2172-2181 (1993)).

Examples of bacteria which can naturally access the cytoplasm of avian cells include, but are not restricted to, *Salmonella galinarum* (ATCC No. 9184), *Salmonella enteriditis* (ATCC No. 4931) and *Salmonella typhimurium* (ATCC No. 6994). Attenuated bacteria are preferred to the present invention and include attenuated *Salmonella* strains such as *S. galinarum* cya crp mutant (Curtiss et al. (1987) supra) or *S. enteritidis* aroA aromatic-dependent mutant CVL30 (Cooper et al. *Infect. Immun.*, 62:4739-4746 (1994)).

Examples of bacteria which can naturally access the cytoplasm of reptilian cells include, but are not restricted to, *Salmonella typhimurium* (ATCC No. 6994). Attenuated bacteria are preferable to the present invention and include, attenuated strains such as *S. typhimuirum* aromatic-dependent mutant (Hormaeche et al. supra).

The present invention also provides for delivery of RNA to other eukaryotic cells, e.g., plant cells, so long as there are microorganisms which are capable of invading such cells, either naturally or after having been modified to become invasive. Examples of microorganisms which can invade plant cells include *Agrobacterium tumerfacium*, which uses a pilus-like structure which binds to the plant cell via specific receptors, and then through a process that resembles bacterial conjugation, delivers at least some of its content to the plant cell.

Set forth below are examples of cell lines to which RNA can be delivered according to the method of this invention.

Examples of human cell lines include but are not limited to ATCC Nos. CCL 62, CCL 159, HTB 151, HTB 22, CCL 2, CRL 1634, CRL 8155, HTB 61, and HTB104.

Examples of bovine cell lines include ATCC Nos. CRL 6021, CRL 1733, CRL 6033, CRL 6023, CCL 44 and CRL 1390. Examples of ovine cells lines include ATCC Nos. CRL 6540, CRL 6538, CRL 6548 and CRL 6546.

Examples of porcine cell lines include ATCC Nos. CL 184, CRL 6492, and CRL 1746.

Examples of feline cell lines include CRL 6077, CRL 6113, CRL 6140, CRL 6164, CCL 94, CCL 150, CRL 6075 and CRL 6123.

Examples of buffalo cell lines include CCL 40 and CRL 6072.

Examples of canine cells include ATCC Nos. CRL 6213, CCL 34, CRL 6202, CRL 6225, CRL 6215, CRL 6203 and CRL 6575.

Examples of goat derived cell lines include ATCC No. CCL 73 and ATCC No. CRL 6270.

Examples of horse derived cell lines include ATCC Nos. CCL 57 and CRL 6583.

Examples of deer cell lines include ATCC Nos. CRL 6193-6196.

Examples of primate derived cell lines include those from chimpanzee's such as ATCC Nos. CRL 6312, CRL 6304, and CRL 1868; monkey cell lines such as ATCC Nos. CRL 1576, CCL 26, and CCL 161; orangautan cell line ATCC No. CRL 1850; and gorilla cell line ATCC No. CRL 1854.

3.1 Cancer Stem Cells and Non-Cancer Stem Cells

Cancer stem cells (CSCs) are a subpopulation of cancer cells that possess characteristics normally associated with stem cells such as self-renewal and the ability to differentiate into multiple cell types. Recent research suggests that CSCs are highly tumorigenic while the bulk of cancer cells are non-tumorigenic. According to these studies, CSCs, while constituting only a small portion of the tumor cells (typically less than 1%), are fundamentally responsible for continued malignant growth and often the initiators of metastasis. CSCs tend to resist chemotherapies and other tumor-targeting therapies currently available in hospitals.

CSCs are also difficult to isolate and, further, to culture for laboratory purposes. Special isolation procedures are required and the cells tend to lose stem-cell characteristics very quickly in culture. Therefore, there is usually only a short window for experimentation with CSCs in vitro. As shown in examples described herein below in the Examples section, methods of the present invention, however, displayed surprising potency and specificity in effecting gene-silencing even in isolated cancer stems cells.

Specifically, bacteria carrying vectors constructed according to the present invention were shown to substantially reduce the expression of the target gene (CSCP1 and CSCP3, respectively). Phenotypic changes in the target cells, e.g., apoptosis (Examples 3 and 4) and spherogenesis inhibition (Example 5), also resulted from treating cells with bacteria of the present invention, offering validation that the targeted genes play important roles in cell survival, division, and death pathways.

With proven capability to effect gene silencing in minute cell populations and in non-culturable cell populations, the TPIV® technology provides a platform for in vitro target/pathway discovery and for devising treatment options in any cell populations including cancer stem cells, and non-cancer stem cells that share some of the CSC's characteristics.

The present invention also provides an example where substantial cell death in non-CSC cancer cells, i.e., "regular" or differentiated cancer cells, resulted from treatment by bacteria of the present invention (Example 6), further confirming the therapeutic potential of the present invention.

4. In Vivo and In Vitro Research and Drug Development

The RNAi methods of the present invention can be used to create transient "knockdown" genetic animal models, e.g., a mouse model, as opposed to genetically engineered knockout models to discover and/or validate gene functions in vivo.

Currently, there is no good system for in vivo target validation. Current knockout animal models are time-consuming, labor-intensive, and require gene targeting in the embryonic stage. Further, current knockout animal models are not feasible to test established tumors in vivo. Current RNAi delivery methods also are not suitable for in vivo target validation. In contrast, the bacteria-mediated RNAi methods of the present invention utilize a system that is suitable for fast and efficient in vivo target validation, e.g., in established tumors. Specifically, bacteria are easier to control and target than viral carriers. Further, the present methods imitate therapeutic-intervention.

For example, transgenic mice with xenografted human tumor can be used as a knockdown animal model to validate the efficacy of a candidate therapy by using the vector and bacteria of the present invention. Such non-pathogenic bacteria, once introduced into the animal model, will produce processed product of non-shRNA, e.g., a mixture of short RNA duplexes against a target gene's mRNA in the tumor cells. This provides a means to conduct gene knockdown analysis and to test anti-tumor activity of a candidate therapy.

In vitro target validation can be accomplished easily using the present invention. In one embodiment, an assay includes the following steps after a target to a phenotype, e.g., cancer growth, has been identified: constructing a vector that encodes a non-shRNA (e.g., long dsRNA) comprising a sequence substantially complementary to the mRNA of that target gene; transforming a live invasive bacterium with the vector; transfecting cancer cells in vitro with the live invasive bacterium; and observe if cell proliferation is affected.

Methods of the present invention can also be used as in vitro transfection tool for research and drug development.

These in vivo and in vitro methods use bacteria with desirable properties (invasiveness, attenuation, steerability). For example, Bifidobacteria and *Listeria*, are used to perform bacteria-mediated RNAi methods of the present invention. Invasiveness as well as eukaryotic or prokaryotic transcription of one or several dsRNAs is conferred to a bacterium using plasmids.

5. Pharmaceutical Compositions

In a preferred embodiment of the invention, the invasive bacteria containing the RNA molecules, and/or DNA encoding such, are introduced into an animal by intravenous, intramuscular, intradermal, intraperitoneally, peroral, intranasal, intraocular, intrarectal, intravaginal, intraosseous, oral, immersion and intraurethral inoculation routes.

The amount of the live invasive bacteria of the present invention to be administered to a subject will vary depending on the species of the subject, as well as the disease or condition that is being treated. Generally, the dosage employed will be about $10^3$ to $10^{15}$ viable organisms, preferably about $10^4$ to $10^{12}$ viable organisms per subject. Bacteria can be prepared in lyophilized, or in spore forms for storage, or pharmaceutical use.

The invasive bacteria of the present invention are generally administered along with a pharmaceutically acceptable carrier and/or diluent. The particular pharmaceutically acceptable carrier an/or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al. *J. Clin. Invest,* 79:888-902 (1987); and Black et al *J. Infect. Dis.,* 155:1260-1265 (1987)), or bicarbonate buffer (pH 7.0) containing ascorbic acid, lactose, and optionally aspartame (Levine et al. *Lancet,* 11:467-470 (1988)). Examples of carriers include proteins, e.g., as found in skim milk, sugars, e.g., sucrose, or polyvinylpyrrolidone. Typically these carriers would be used at a concentration of about 0.1-30% (w/v) but preferably at a range of 1-10% (w/v).

Set forth below are other pharmaceutically acceptable carriers or diluents which may be used for delivery specific routes. Any such carrier or diluent can be used for administration of the bacteria of the invention, so long as the bacteria are still capable of invading a target cell. In vitro or in vivo tests for invasiveness can be performed to determine appropriate diluents and carriers. The compositions of the present invention can be formulated for a variety of types of administration, including systemic and topical or localized administration. Lyophilized forms are also included, so long as the bacteria are invasive upon contact with a target cell or upon administration to the subject. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the composition, e.g., bacteria, of the present invention can be formulated in liquid solutions, preferably in physiologically compatible buffers such as Hank's solution or Ringer's solution.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

For administration by inhalation, the pharmaceutical compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition, e.g., bacteria, and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain fomiulatory agents such as suspending, stabilizing and/or dispersing agents. Alternatively, the active ingredient may be in powder form for constitution with a suitable vehicle, e.g., sterile pyrogen-free water, before use.

The pharmaceutical compositions may also be formulated in rectal, intravaginal or intraurethral compositions such as suppositories or retention enemas, e.g., containing conventional suppository bases such as cocoa butter or other glycerides. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the bacteria of the present invention are formulated into ointments, salves, gels, or creams as generally known in the art, so long as the bacteria are still invasive upon contact with a target cell.

The compositions may, if desired, be presented in a pack or dispenser device and/or a kit which may contain one or more unit dosage forms containing the active ingredient. The pack may, for example, comprise metal or plastic foil, such as a blister pack. The pack or dispenser device may be accompanied by instructions for administration.

The invasive bacteria containing the RNA or RNA-encoding DNA to be introduced can be used to infect animal cells that are cultured in vitro, such as cells obtained from a subject. These in vitro-infected cells can then be introduced into animals, e.g., the subject from which the cells were obtained initially, intravenously, intramuscularly, intradermally, or intraperitoneally, or by any inoculation route that allows the cells to enter the host tissue. When delivering RNA to individual cells, the dosage of viable organisms administered will be at a multiplicity of infection ranging from about 0.1 to $10^6$, preferably about $10^2$ to $10^4$ bacteria per cell.

In yet another embodiment of the present invention, bacteria can also deliver RNA molecules encoding proteins to cells, e.g., animal cells, from which the proteins can later be harvested or purified. For example, a protein can be produced in a tissue culture cell.

6. Therapeutic and Prophylactic Uses

The RNAi methods of the present invention can be used for the treatment and/or prevention of various diseases, including the diseases summarized in Dykxhoorn, Novina & Sharp. *Nat. Rev. Mol. Cell. Biol.* 4:457-467 (2003); Kim & Rossi, *Nature Rev. Genet.* 8:173-184 (2007); de Fougerolles, et al. *Nature Rev. Drug Discov.* 6:443-453 (2007).

In an embodiment, the present invention can be used as a cancer therapy or to prevent cancer. This method is effected by silencing or knocking down genes involved with cell proliferation or other cancer phenotypes. The bacteria of the present invention used for cancer treatment is preferably bacteria engineered to safely seek out and kill tumors (Forbes, *Nature Biotechnology* 24:1484-1485 (2006)). The bacteria can be an obligate anaerobe, such as *Clostridium novyi*-NT, or facultative anaerobe, such as *Salmonella typhimurium* and *Escherichia coli*. (ibid)

Examples of these genes are k-Ras and β-catenin. Specifically, k-Ras and β-catenin are targets for RNAi based therapy of colon cancer. These oncogenes are active and relevant in the majority of clinical cases. The bacteria-mediated RNAi methods of the present invention are applied to reach the intestinal tract for colon cancer treatment and prevention. These methods are also used to treat animals carrying xenograft tumors, to treat and prevent cancer in k-RasV12 model of intestinal tumorgenesis, and to prevent and treat tumors in the adenomatous polyposis coli min mouse model (APC-min model). In this model, the mouse has a defective APC gene resulting in the formation of numerous intestinal and colonic polyps which is used as an animal model for human familiar adenomatous polyposis coli (FAP) of intestinal tumorigenesis.

The RNAi methods of the invention can also be used to treat or prevent viral diseases (e.g. hepatitis) and genetic disorders.

The RNAi methods of the present invention can also be used to create cancer-preventing "probiotic bacteria" for use, especially with the target of GI tract or liver. The RNAi methods of the present invention are used as therapy against inflammatory conditions, e.g. hepatitis, inflammatory bowel disease (IBD) or colitis. These methods are used to silence or knockdown non-cancer gene targets (viral genes, for treatment and prevention of hepatitis B, C; inflammatory genes, for treatment and prevention of inflammatory bowel disease) and others.

The RNAi methods of the present invention can be used for delivery of gene silencing to the gut and colon, and for oral application in the treatment of various diseases, namely colon cancer treatment and prevention. In another aspect of this embodiment, delivery of gene silencing is extra-intestinal.

The bacteria produced and/or delivered dsRNA can be used for the treatment of viral infection, such as HIV, HBV, HCV or other diseases where a specific disease-causing gene can be identified. Because the present invention does not require identification of the precise siRNA sequence that is effective against a specific disease-causing gene, whether that gene is endogenous or viral, methods of the present invention are particularly advantageous against treating disease genes that mutate frequently or have a lot of sub-genotypes or strains. A classic example is HIV which carry genes that mutate frequently.

7. TPIV® Library

The invention also provides a RNAi library, called a "TPIV® library," which can be genome-wide or gene-family-specific. TPIV® library is a randomly constructed, double-stranded, auto-pooled, size controllable RNAi library. The in-vitro cell system RNAi library screening is based on the bacterial RNAi system of the present invention, and microscopic imaging analysis. Compared to current siRNA/shRNA libraries which require prior knowledge of "good" siRNA sequences and have limited applications to certain cell types (e.g., dividing cells and cells with viral receptors), the TPIV® libraries of the present invention can target both known and unknown genes, and apply to a broad range of cell types. Moreover, the TPIV® libraries of the present invention are suitable for in vivo validation.

Figure 2:
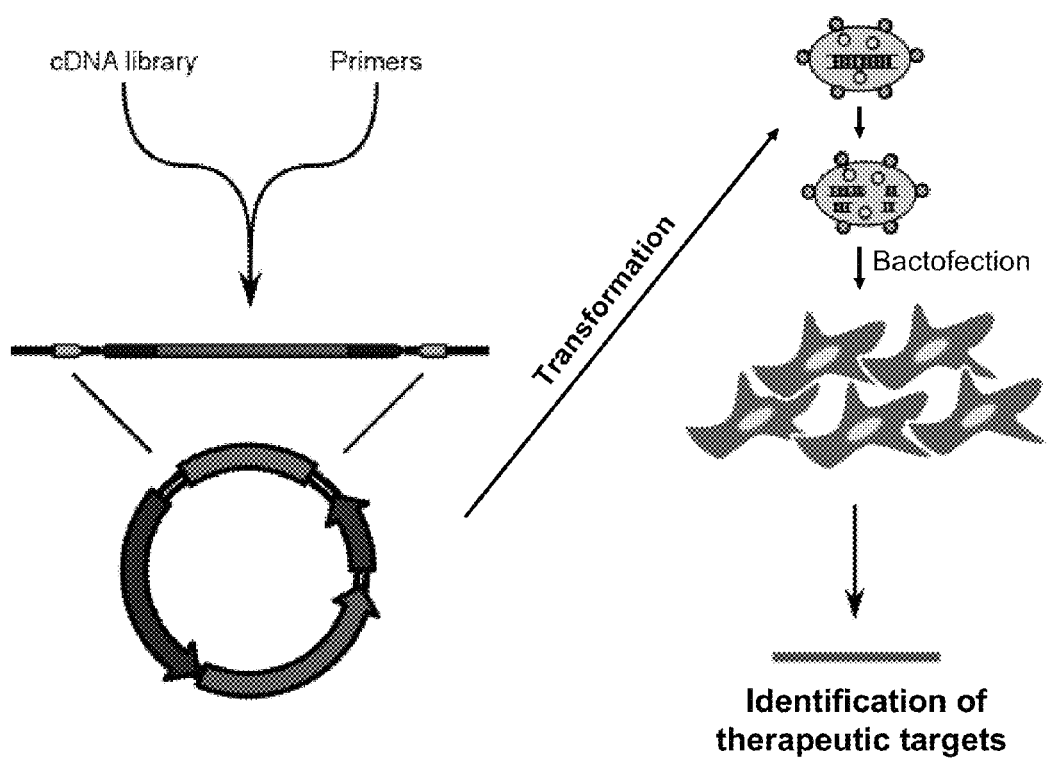
FIG. 2 is a schematic diagram showing how a TPIV® library can be constructed and utilized according to an embodiment of the present invention.

Referring to FIG. 2, in an embodiment, the TPIV® library of the present invention comprises a plurality of vectors, each vector comprising one cDNA molecule from a cDNA library or a cDNA fragment, a first promoter, and a second promoter; wherein the first promoter controls the expression of one strand of the cDNA molecule or a cDNA fragment, and the second promoter controls the expression of the other strand of the cDNA molecule or a cDNA fragment. The cDNA fragments can be obtained from enzyme digestion of cDNA molecules. In one embodiment, cDNA fragments of about 500 bp were generated through enzyme digestion. The constructed vectors can be used to transform bacterial cells. Once the vector transcribes a dsRNA from the cDNA sequence or the cDNA fragment, the bacterial cell processes the dsRNA into a mixture of shorter RNA duplexes as described herein previously. After bactofection into target cells, cells exhibiting expected phenotypic changes can be selected for further identification of the genetic target. The cDNA pool or library can be derived from total mRNA from mammalian cells, or mRNAs from a gene family or a gene.

The present invention further provides a method of screening an RNAi library. The method comprises infecting mammalian cells with the TPIV® library, and identifying the mammalian cells with at least one phenotypic change. The at least one phenotypic change is selected from the group consisting of numbers of nuclei, nuclei morphology, cell death, cell proliferation, DNA fragmentation, cell surface marker, and mitotic index. The method can further comprise sequencing the cDNA molecule of the vector within the identified mammalian cells.

RNAi library can be used to screen disease-related drug targets in large-scale and validate potential therapeutic molecular drug target. It can be used to assess the functions of all human genes and to conduct functional genomic experiments without knowing a priori which genes to target. It can also be used to conduct unbiased analyses in relevant cellular assays across different disease states and derive multidimensional relationships of gene function in disease.

The RNAi libraries currently used in the field include pooled chemically synthesized siRNA library, viral vector-based shRNA library; and double-strand RNA (dsRNA) in-vitro digested mixture. These libraries need to be constructed or synthesized one by one against known genes. They are usually size-limited, and most of them are even not renewable. While screening, these libraries need to be transfected into cell system.

The present invention provides an easy way to create and screen RNAi library. It simplifies the library construction process. To build a RNAi library, plasmids need not to be constructed one by one. The present invention also eliminates the time-consuming and tedious products purification steps. Moreover, the present invention can directly deliver RNAi through bacterial infection, thereby greatly reduced the library screening cost.

TPIV® library can be whole genome or gene family feasible. For each target, it has an auto-pooled mixture of short RNA duplexes rather than a single siRNA. Thus, there is no need to synthesize siRNAs one by one, and no need to verify the effective sequence for siRNA. (Zhao H F, et al, Nature Methods 2:967-973 (2005)). The present invention can avoid N-terminal function, and thereby lead to complete function knockdown. The screening of TPIV® library is selection-based double blind screening, and unbiased, i.e., genetic information is balanced well. In addition, it is easy to track back to find the candidate gene using TPIV® library. In one embodiment, the TPIV® library can be used to screen different cancer-related targets in transgenic as well as wild type animals for therapeutic experiments.

The present invention is further illustrated by the following examples which should not be construed as limiting in any way. The contents of all cited references including literature references, issued patents, published patent applications as cited throughout this application are hereby expressly incorporated by reference, but they are not admitted to be prior art to presently claimed invention. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Examples are provided below to further illustrate different features of the present invention. The examples also illustrate useful methodology for practicing the invention. These examples do not limit the claimed invention.

Material and Method:

TPIV® Plasmid

Figure 3:
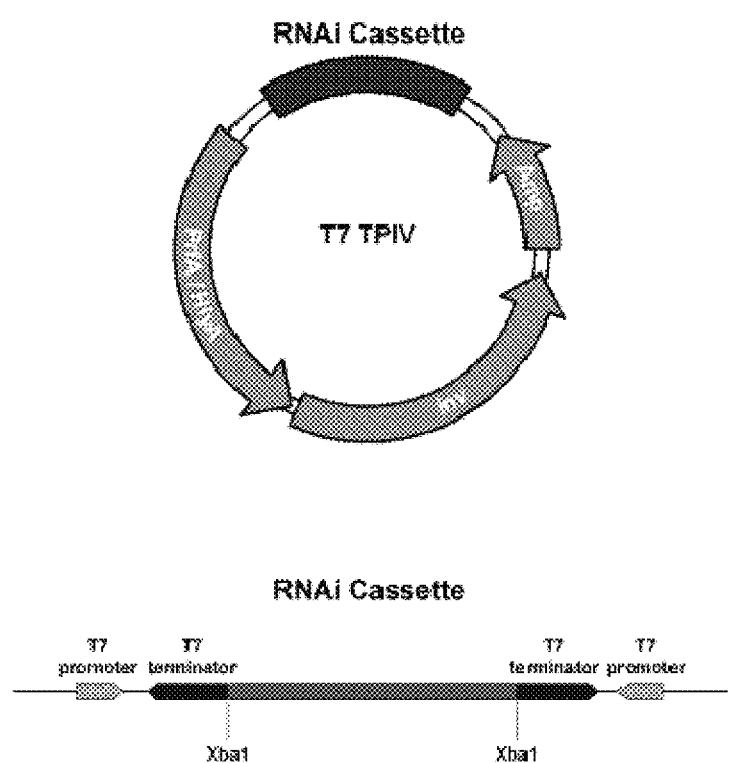
FIG. 3 is a schematic diagram of a double-strand TPIV® plasmid (T7 TPIV®) constructed according to an embodiment of the invention.

Referring to FIG. 3, the T7 TPIV® plasmid was constructed to include an RNAi cassette with two T7 promoters. The desired DNA molecule is cloned into the plasmid through the two XbaI sites.

For example, the CSCP3/STAT3 and CSCP1/beta-catenin plasmids were purchased from Origene Technologies. Either the 782 bp fragment (from nucleotide position 1 to 782), of the human STAT3 gene (GenBank accession no. NM_139276) or an about 300 bp fragment (from nucleotide position 11 to 311) of the CSCP3/STAT3 was inserted into the RNAi cassette. The particular CSCP3-TPIV® plasmid construct used in the following examples contained the 300 bp fragment of the CSCP3/STAT3 gene, which was cloned into the base TPIV® plasmid using the following primers:

```
CSCP3/STAT3-TPIV For
                                      (SEQ ID NO: 1)
5'-GGATCTAGAATCAGCTACAGCAGC-3'

CSCP3/STAT3-TPIV Rev
                                      (SEQ ID NO: 2)
5'-TCCTCTAGAGGGCAATCTCCATTG-3'
```

For the CSCP1/beta-catenin-TPIV® plasmid, a 567 bp fragment (from nucleotide position 215 to 783) of the full-length human beta-catenin gene (GenBank accession no. NM_001904) was inserted into the RNAi cassette of the T7-TPIV® plasmid using standard molecular cloning techniques.

For vector construction, T7 Terminators were annealed according to standard molecular biology techniques, and digested with either BamHI/XbaI or XbaI/SalI. Terminators were then cloned into the BamHI/XbaI or XbaI/SalI sites of the TPIV® vector using the following primers:

BamHI sense:
(SEQ ID NO: 3)
5'ACGGATCCTCCTTTCAGCAAAAAACCCCTCAAGACCCGTTTAGAGGCC

CCAAGGGGTTATGCTAGTTATTGCTCAGCGGTGGTCTAGAGGATCCAC

3'

BamHI antisense:
(SEQ ID NO: 4)
5'GTGGATCCTCTAGACCACCGCTGAGCAATAACTAGCATAACCCCTTGG

GGCCTCTAAACGGGTCTTGAGGGGTTTTTGCTGAAAGGAGGATCCGT

3'

SalI sense:
(SEQ ID NO: 5)
5'GCGTCGACTCTAGACCACCGCTGAGCAATAACTAGCATAACCCCTTGG

GGCCTCTAAACGGGTCTTGAGGGGTTTTTGCTGAAAGGAGTCGACCG

3'

SalI antisense:
(SEQ ID NO: 6)
5'CGGTCGACTCCTTTCAGCAAAAAACCCCTCAAGACCCGTTTAGAGGCC

CCAAGGGGTTATGCTAGTTATTGCTCAGCGGTGGTCTAGAGTCGACGC

3'

CSC Isolation

Figure 4:
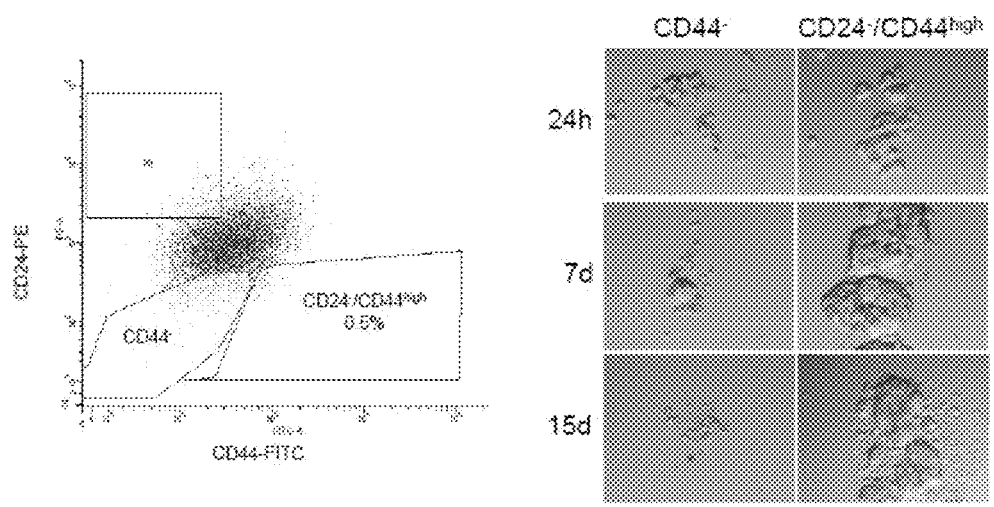
FIG. 4 includes a FACS diagram in the left panel and microscopic images in the right panel, illustrating isolation of cancer stem cells (CSCs) according to an embodiment of the present invention.

Cancer stem cells (CSCs) were isolated by selecting for the existence of certain surface markers such as CD44 and for the absence of certain other surface markers such as CD24. Referring to FIG. 4, CD44$^-$ cells and CD24$^-$/CD44$^{high}$ cells were isolated from FaDu human head and neck cancer cell by florescence-activated cell sorting (FACS) (left panel). The cells were then cultured in the absence of attachment and serum for the indicated time period to test their ability to form spheres (right panel).

Micrographic Images in the right panel indicates that CD44$^-$ cells did not have the capability to form spheres while CD24$^-$/CD44$^{high}$ cells did, confirming that CD24$^-$/CD44$^{high}$ cells were indeed cancer stem cells.

Example 1

RNAi Against CSCP1 in Cancer Stem Cells (CSCs)

Figure 5:
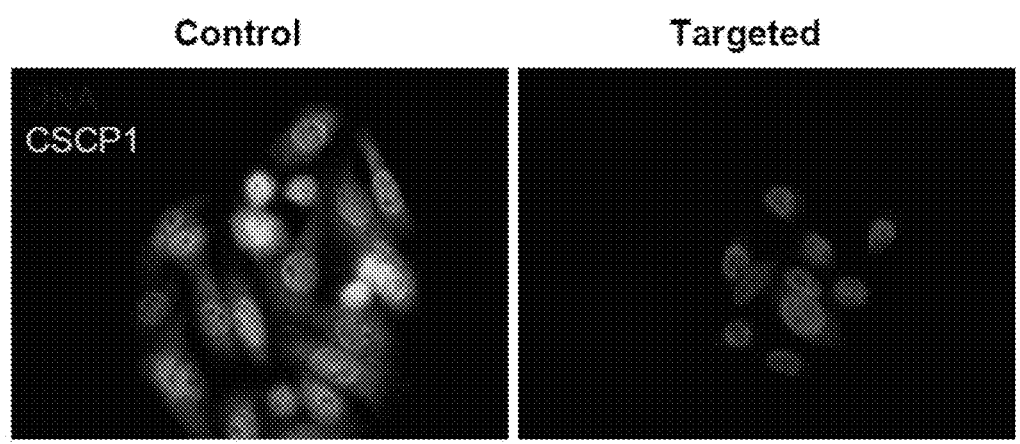
FIG. 5 show immunofluorescent images of CSCP1 protein expression analysis in CSCs treated with bacteria of the present invention targeting CSCP1 (right panel) and control (left panel).

Selected from side population, SW480 human colon cancer Hoechst side population (SP) cancer stem cells were treated with *E. coli* cells, BL21 (DE3) pLysE, that carry the CSCP1-TPIV® plasmid described above. Control cancer stem cells were treated with bacteria carrying control TPIV® plasmid. Forty-eight hours after bacterial entry, cells were fixed and stained for CSCP1/beta-catenin protein by standard immunofluorescent techniques. Control cells (FIG. 5, left panel) contained normal levels of CSCP1/beta-catenin while CSCP1-targeting bacteria triggered specific loss of CSCP1/beta-catenin through RNAi (right panel).

Example 2

RNAi Against CSCP3 in Cancer Stem Cells (CSCs) Selected by Side Population

Figure 6:
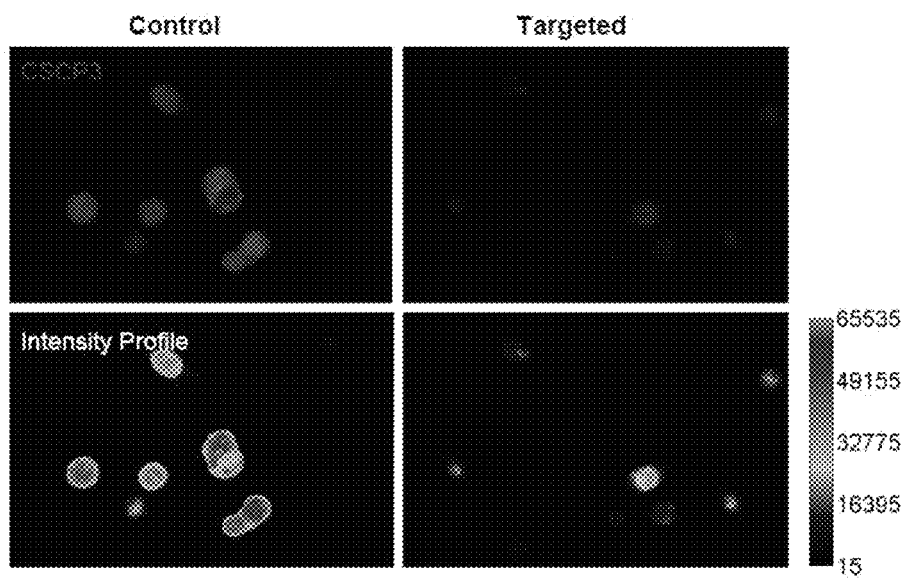
FIG. 6 includes single-channel images (top panels) and intensity profiles (bottom panels) of CSCP3 protein expression analysis in CSCs treated with bacteria of the present invention targeting CSCP3 (right panels) and controls (left panels).

SW480 human colon cancer Hoechst side population (SP) cancer stem cells prepared as in Example 1, were treated with *E. coli* cells, BL21 (DE3) pLysE, that carry CSCP3-TPIV® plasmid. Twenty-four hours after bacterial entry, cells were fixed and stained for CSCP3/STAT3 protein using standard immunofluorescent techniques. In FIG. 6, the top two panels show single-channel immunofluorescent images. Bottom two panels show intensity profile of CSCP3 with pixel intensity scale provided in the far right. Cells treated with bacteria targeting CSCP3/STAT3 (right panels) show decreased levels of CSCP3/STAT3, proving that RNAi was effectively carried out through the present bacteria-mediated system.

Example 3

RNAi Against CSCP3 Caused Apoptosis in Cancer Stem Cells (CSCs)

Figure 7:
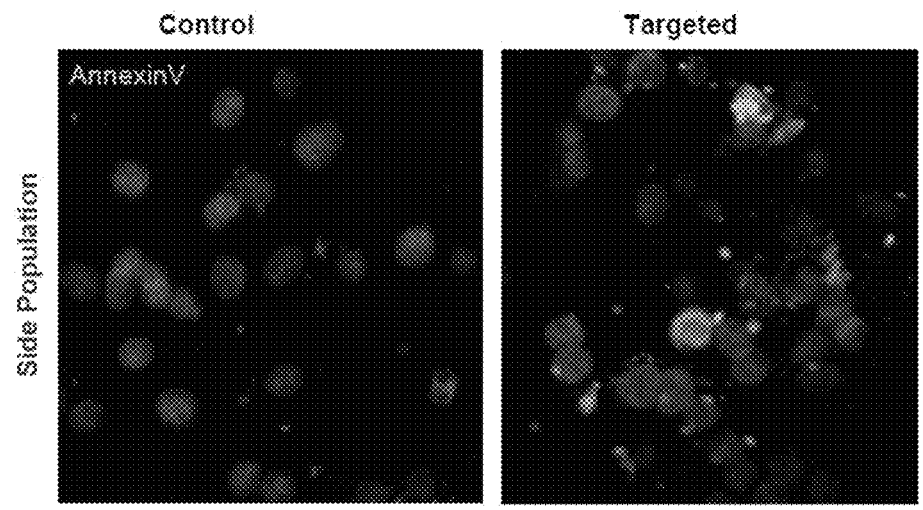
FIG. 7 includes microscopic images of Annexin V-FITC staining assay in CSC populations treated with bacteria of the present invention targeting CSCP3 (right panel) and control (left panel).

The same cells as in Example 2 and similarly treated were fixed and stained with Annexin V-FITC 24 hours after bacterial entry in order to identify apoptotic (Annexin V positive) cells. As shown in FIG. 7, significant numbers of cells treated with CSCP3-TPIV® became apoptotic (right panel) while control cells remained healthy (left panel). This shows the therapeutic potential of using the present invention to treat cancer stem cells and cancer in general.

Example 4

RNAi Against CSCP3 in Cancer Stem Cells (CSCs) Selected by Surface Marker

Figure 8:
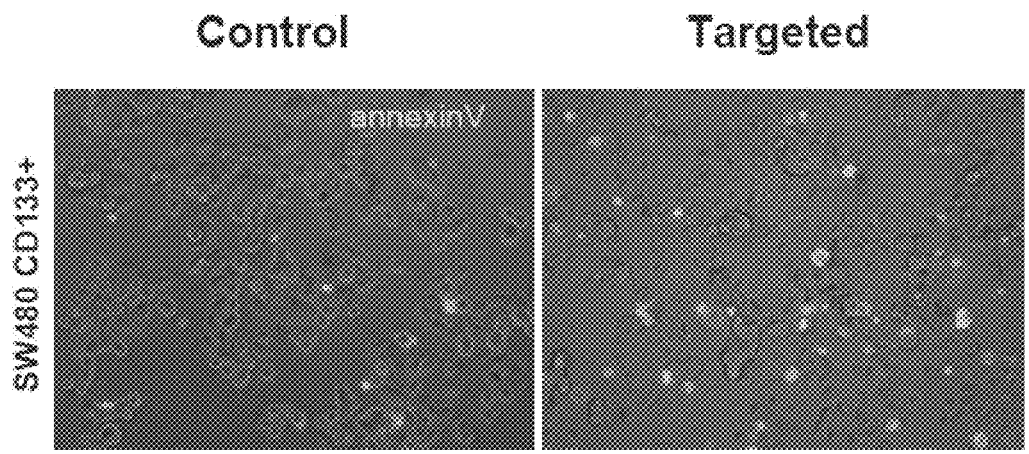
FIG. 8 shows another set of microscopic images of Annexin V-FITC staining assay in CSC populations treated with bacteria of the present invention targeting CSCP3 (right panel) and control (left panel).

Cancer stem cells were selected by surface marker CD133 using FACS. The resulting SW480 human colon cancer CD133$^+$ cancer stem cells were then treated with CSCP3-TPIV® or control TPIV®. After 24 hours, cells were fixed and stained with Annexin V-FITC to identify apoptotic cells. Similar results to Example 3 were observed as significantly more cells treated with CSCP3-TPIV® (FIG. 8, right panel) became apoptotic than the control (left panel).

Example 5

RNAi Against CSCP3 Inhibited Sphere Formation in Cancer Stem Cells (CSCs)

Figure 9:
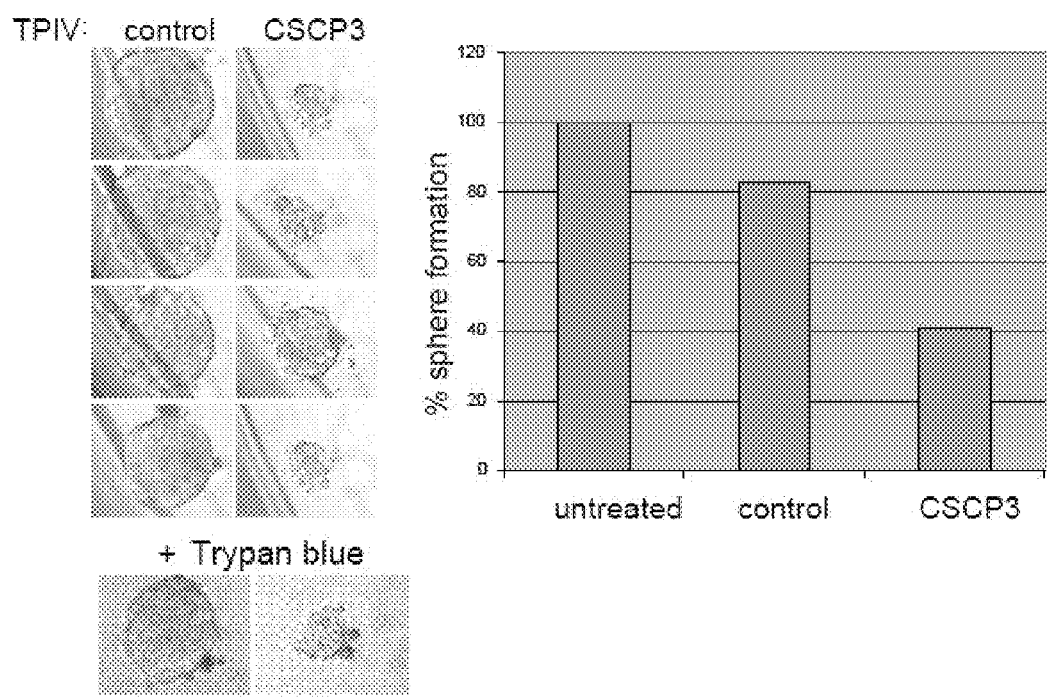
FIG. 9 includes microscopic images of spheres of CSCs treated with bacteria of the present invention targeting CSCP3 before trypan blue was added (top left panels) and after trypan blue was added (bottom left panel). The chart on the right illustrates quantitatively the effect of bacteria of the present invention on the CSC populations pictured on the left.

CSCP3/STAT3 RNA silencing using methods of the present invention also inhibited spherogenesis of CSCs by as much as 60% (FIG. 9, right panel). CD44$^{high}$ FaDu cells isolated through FACS were treated with CSCP3-TPIV® or control TPIV. Then, the cells were cultured in the absence of attachment and serum for 5 days to form spheres. Representative sphere images were captured before (left upper panels) or after the addition of trypan blue to identify dead cells (left bottom panel). Sphere growth was scored by counting the number of spheres possessing more than 50 cells.

Example 6

RNAi Against CSCP3 in Non-CSC Cells

Figure 10:
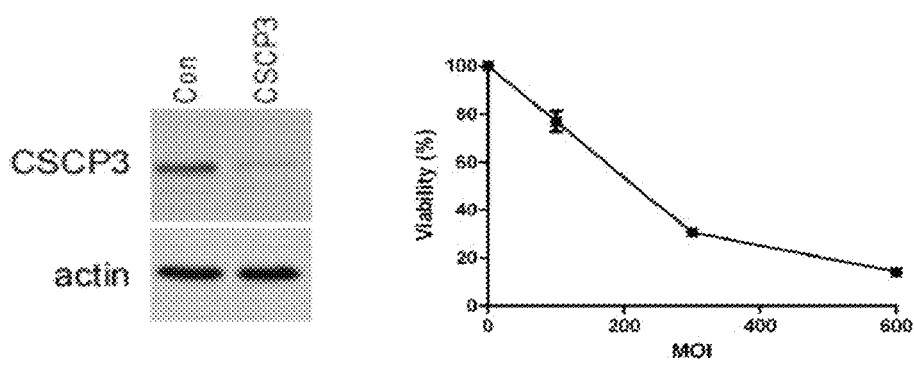
FIG. 10 includes a western blot image of CSCP3 protein expression on the left and a chart on the right showing viability statistics from differentiated cancer cells after being treated with the bacteria of the present invention targeting CSCP3, according to one experiment.

U2OS human osteosarcoma cells were treated with CSCP3-TPIV® or control TPIV® plasmids. Cells were harvested and levels of CSCP3/STAT3 protein were determined by western blot analysis at 24 hours post bacterial infection (FIG. 10, left panel). The viability of the cells was determined by a regular MTT assay (right panel) 72 hours after the treatment, which shows 70% mortality among the cancer cells at MOI of 300 and over 80% cell mortality at MOI of 600. This provides evidence of high efficacy of bacteria-mediated RNAi methods of the present invention against differentiated, non-stem cancer cells.

Other embodiments are within the following claims. While several embodiments have been shown and described, various modifications may be made without departing from the spirit and scope of the present invention.

Sequence listings and related materials in the ASCII text file named "SEQLISTING_US002.txt" and created on Dec. 13, 2010 with a size of about 2 kilobytes, is hereby incorporated by reference.

What is claimed is:

1. A method of substantially reducing gene expression in a target eukaryotic cell, the method comprising:
infecting a eukaryotic host with a plurality of bacteria, each bacterium comprising an exogenous long double-strand RNA (dsRNA), or a DNA molecule encoding RNA molecules that form the long dsRNA, and an enzyme or ribozyme capable of processing the long dsRNA into a mixture of shorter RNA duplexes capable of regulating a target gene expression, wherein the long dsRNA comprises a sequence substantially complementary to a messenger RNA (mRNA) sequence encoded by said target gene, or the DNA is one complementary DNA (cDNA) molecule from a cDNA library or a fragment thereof, wherein the long dsRNA is a non-short-hairpin RNA, and wherein the double-stranded region of the long dsRNA is longer than 70 bp, allowing the plurality of bacteria to transcribe and process, within a target eukaryotic cell, the long dsRNAs into the mixture of shorter RNA duplexes, producing a randomly constructed, double-stranded RNAi library;
thereby delivering said RNAi library, via said plurality of bacteria, into target eukaryotic cells without triggering significant immune response from said eukaryotic host, and substantially reducing said target gene expression.

2. The method of claim 1, wherein said target gene is a eukaryotic gene or viral gene.

3. The method of claim 1, further comprising producing and processing said long dsRNA inside said bacterium, and lysing said bacterium to release its content.

4. The method of claim 3 wherein the content of said bacterium is further processed in said target eukaryotic cell to become said mixture of shorter RNA duplexes.

5. The method of claim 1 wherein said bacterium is capable of processing said long dsRNA into said mixture of shorter RNA duplexes before releasing its content.

6. The method of claim 1 wherein said enzyme is an endonuclease.

7. The method of claim 1 wherein said enzyme comprises a bacterial RNase III, a Dicer, or a Dicer-like enzyme.

8. The method of claim 1 wherein the long dsRNA is at least of a length selected from the group consisting of 100, 200, 400 and 1000 bp.

9. The method of claim 1 wherein said DNA molecule comprises a prokaryotic promoter controlling the expression of said long dsRNA.

10. The method of claim 9 wherein said prokaryotic promoters is a T7 promoter.

11. The method of claim 9 wherein said prokaryotic promoters is endogenous to said bacterium.

12. The method of claim 1 wherein said DNA molecule comprises two prokaryotic promoters controlling the expression of the two strands of said DNA molecule.

13. The method of claim 1 wherein said target gene is an animal gene or a plant gene.

14. The method of claim 1 wherein said target gene is a mammalian gene or an avian gene.

15. The method of claim 1 wherein said target gene is a mammalian disease gene.

16. The method of claim 1 wherein said target gene is a cancer gene.

17. The method of claim 1 wherein said target gene is β-catenin, k-Ras or HIV.

18. The method of claim 1 wherein said bacterium is invasive.

19. The method of claim 1 wherein said bacterium is live or half-killed.

20. The method of claim 1 wherein said bacterium is non-pathogenic.

21. The method of claim 1, wherein said bacterium is an attenuated strain selected from the group consisting of Listeria, Shigella, Salmonella, E. coli, Agrobacterium tumerfacium and Bifidobacteriae.

22. The method of claim 1 wherein said DNA molecule comprises a circular, double-strand plasmid.

23. The method of claim 1 wherein the DNA molecule is integrated into a bacterial chromosome.

24. The method of claim 1 wherein said long dsRNA comprises a sequence that is perfectly complementary to the mRNA sequence of said target gene.

25. The method of claim 1, wherein said bacterium further comprises a second enzyme that assists in transporting genetic materials, upon their release from said bacterium, into the cytoplasm of said target eukaryotic cell.

26. The method of claim 25 wherein said second enzyme is an Hly protein.

27. The method of claim 1, wherein said cDNA library is derived from total mRNA from a mammalian cell.

28. The method of claim 1, wherein said cDNA library is derived from mRNAs from a gene family or a gene.

* * * * *